(12) United States Patent
Kaylor et al.

(10) Patent No.: US 7,244,393 B2
(45) Date of Patent: Jul. 17, 2007

(54) DIAGNOSTIC DEVICE AND SYSTEM

(75) Inventors: Rosann Marie Kaylor, Cumming, GA (US); Chibueze O. Chidebelu-Eze, Atlanta, GA (US); Robert John Lyng, Alpharetta, GA (US); Stephen Quirk, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 394 days.

(21) Appl. No.: 10/026,415

(22) Filed: Dec. 21, 2001

(65) Prior Publication Data

US 2003/0118480 A1 Jun. 26, 2003

(51) Int. Cl.
 *G01N 33/48* (2006.01)
(52) U.S. Cl. ............................ 422/58; 422/61; 436/165
(58) Field of Classification Search ................. 422/58, 422/61; 436/164, 166, 165
See application file for complete search history.

(56) References Cited

U.S. PATENT DOCUMENTS

| | | | |
|---|---|---|---|
| 4,366,241 A | 12/1982 | Tom et al. | |
| 4,647,544 A | 3/1987 | Nicoli et al. | |
| 4,992,385 A | 2/1991 | Godfrey | |
| 5,196,350 A | 3/1993 | Backman et al. | |
| 5,223,220 A | 6/1993 | Fan et al. | |
| 5,248,479 A | 9/1993 | Parsons et al. | |
| 5,252,459 A | 10/1993 | Tarcha et al. | |
| 5,508,171 A | 4/1996 | Walling et al. | |
| 5,512,131 A | 4/1996 | Kumar et al. | |
| 5,534,132 A | 7/1996 | Vreeke et al. | |
| 5,638,828 A | 6/1997 | Lauks et al. | |
| 5,653,243 A | 8/1997 | Lauks et al. | |
| 5,666,967 A | 9/1997 | Lauks et al. | |
| 5,670,381 A | 9/1997 | Jou et al. | |
| 5,779,650 A | 7/1998 | Lauks et al. | |
| 5,837,454 A | 11/1998 | Cozzette et al. | |
| 5,842,787 A | 12/1998 | Kopf-Sill et al. | |
| 5,872,713 A * | 2/1999 | Douglas et al. | ............... 702/85 |
| 5,922,550 A | 7/1999 | Everhart et al. | |
| 5,948,695 A * | 9/1999 | Douglas et al. | ............. 436/518 |
| 5,968,839 A | 10/1999 | Blatt et al. | |

(Continued)

FOREIGN PATENT DOCUMENTS

WO 94/13835 6/1994

(Continued)

OTHER PUBLICATIONS

Article—*Formation of Droplets and Mixing in Multiphase Microfluidics at Low Values of the Reynolds and the Capillary Numbers*, Joshua D. Tice, Helen Song, Adam D. Lyon, and Rustem F. Ismagilov, Langmuir, vol. 19, No. 22, 2003, pp. 9127-9133.

*Primary Examiner*—Lyle A. Alexander
(74) *Attorney, Agent, or Firm*—Dority & Manning, P.A.

(57) ABSTRACT

Diagnostic devices, systems and methods for detecting the presence of an analyte in a sample are provided. In one embodiment, the device comprises a substrate, a binder printed in a pattern onto a surface of the substrate, and a means for directing a sample towards the surface of the substrate that is printed with the binder. Systems of the present invention further include a light source that can be directed through the aforementioned means or another opening to the binder-printed surface to test for diffraction.

18 Claims, 15 Drawing Sheets

U.S. PATENT DOCUMENTS

| | | |
|---|---|---|
| 6,010,463 A | 1/2000 | Lauks et al. |
| 6,020,047 A | 2/2000 | Everhart |
| 6,030,827 A | 2/2000 | Davis et al. |
| 6,048,623 A | 4/2000 | Everhart et al. |
| 6,057,165 A | 5/2000 | Mansour |
| 6,060,256 A | 5/2000 | Everhart et al. |
| 6,063,589 A | 5/2000 | Kellogg et al. |
| 6,066,448 A * | 5/2000 | Wohlstadter et al. .......... 435/6 |
| 6,096,268 A * | 8/2000 | Inbar ........................... 422/56 |
| 6,143,247 A | 11/2000 | Sheppard, Jr. et al. |
| 6,143,248 A | 11/2000 | Kellogg et al. |
| 6,162,639 A * | 12/2000 | Douglas ................. 435/287.1 |
| 6,180,288 B1 | 1/2001 | Everhart et al. |
| 6,221,579 B1 | 4/2001 | Everhart et al. |
| 6,241,863 B1 | 6/2001 | Monbouquette |
| 6,270,637 B1 | 8/2001 | Crismore et al. |
| 6,281,006 B1 | 8/2001 | Heller et al. |
| 6,294,392 B1 | 9/2001 | Kuhr et al. |
| 6,306,273 B1 | 10/2001 | Wainright et al. |
| 6,379,883 B2 | 4/2002 | Davis et al. |
| 6,399,295 B1 | 6/2002 | Kaylor et al. |
| 6,416,642 B1 | 7/2002 | Alajoki et al. |
| 6,436,651 B1 | 8/2002 | Everhart et al. |
| 6,461,496 B1 | 10/2002 | Feldman et al. |
| 6,481,453 B1 | 11/2002 | O'Connor et al. |
| 6,509,085 B1 | 1/2003 | Kennedy |
| 6,514,399 B1 | 2/2003 | Parce et al. |
| 6,573,040 B2 | 6/2003 | Everhart et al. |
| 6,579,673 B2 | 6/2003 | McGrath et al. |
| 6,582,662 B1 | 6/2003 | Kellogg et al. |
| 6,632,629 B2 | 10/2003 | Yang et al. |
| 6,663,833 B1 | 12/2003 | Stave et al. |
| 6,686,184 B1 | 2/2004 | Anderson et al. |
| 6,742,399 B2 | 6/2004 | Weigle et al. |
| 6,742,661 B1 | 6/2004 | Schulte et al. |
| 6,750,053 B1 | 6/2004 | Widrig Opalsky et al. |
| 2003/0107740 A1 | 6/2003 | Kaylor et al. |
| 2003/0118479 A1 | 6/2003 | Quirk et al. |
| 2003/0119209 A1 | 6/2003 | Kaylor et al. |
| 2003/0207253 A1 | 11/2003 | Kaylor et al. |

FOREIGN PATENT DOCUMENTS

| | | |
|---|---|---|
| WO | 97/03347 | 1/1997 |
| WO | 98/27417 | 6/1998 |
| WO | 98/43086 | 10/1998 |
| WO | 99/31486 | 6/1999 |
| WO | 00/34616 | 6/2000 |
| WO | 00/34781 | 6/2000 |
| WO | 01/44813 | 6/2001 |
| WO | 01/84153 A2 | 11/2001 |
| WO | WO 0181921 | 11/2001 |

* cited by examiner

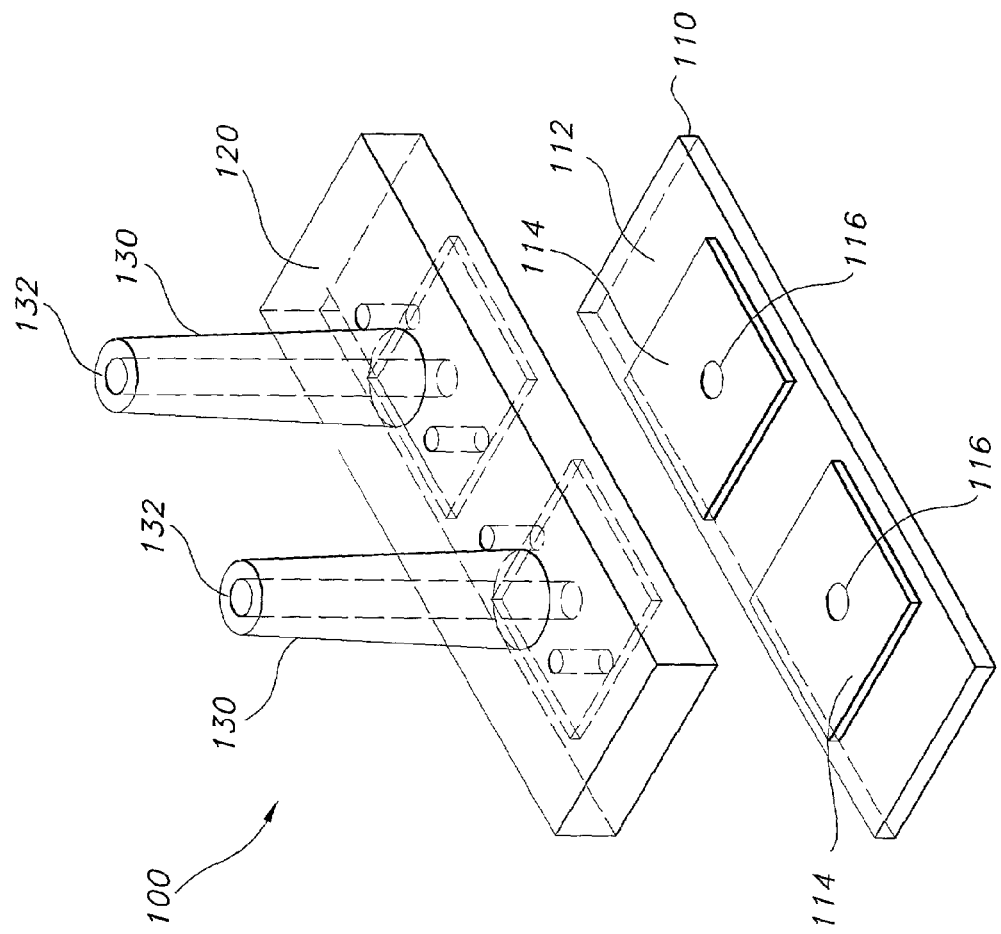

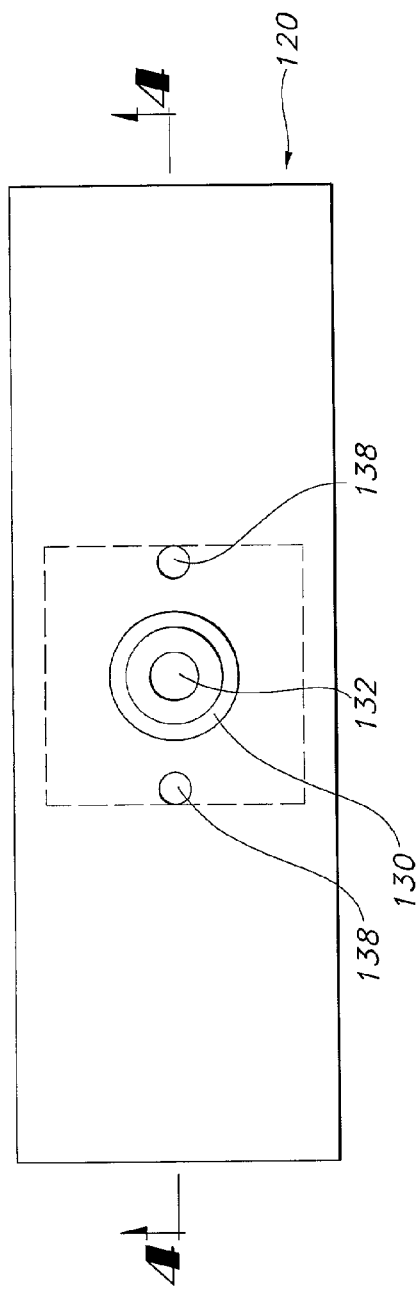
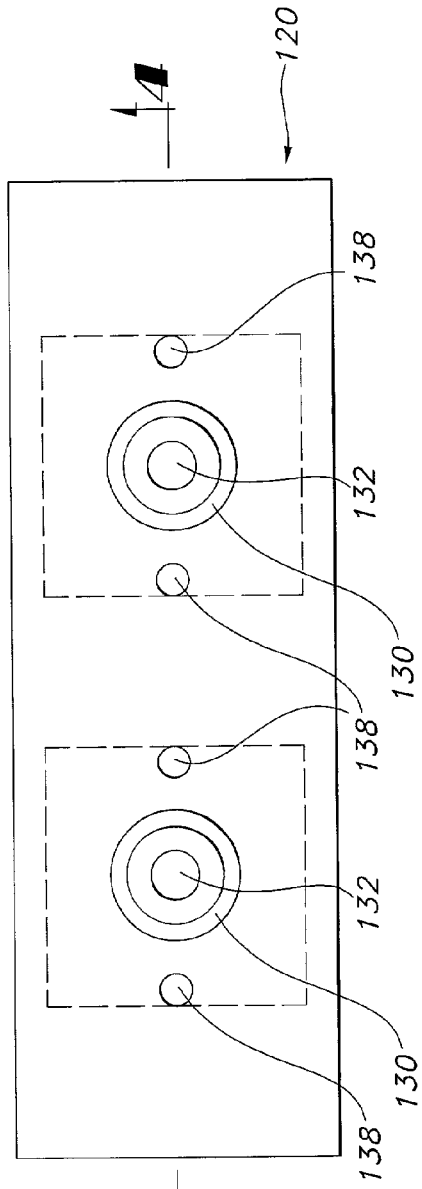
FIG 3
FIG 3A

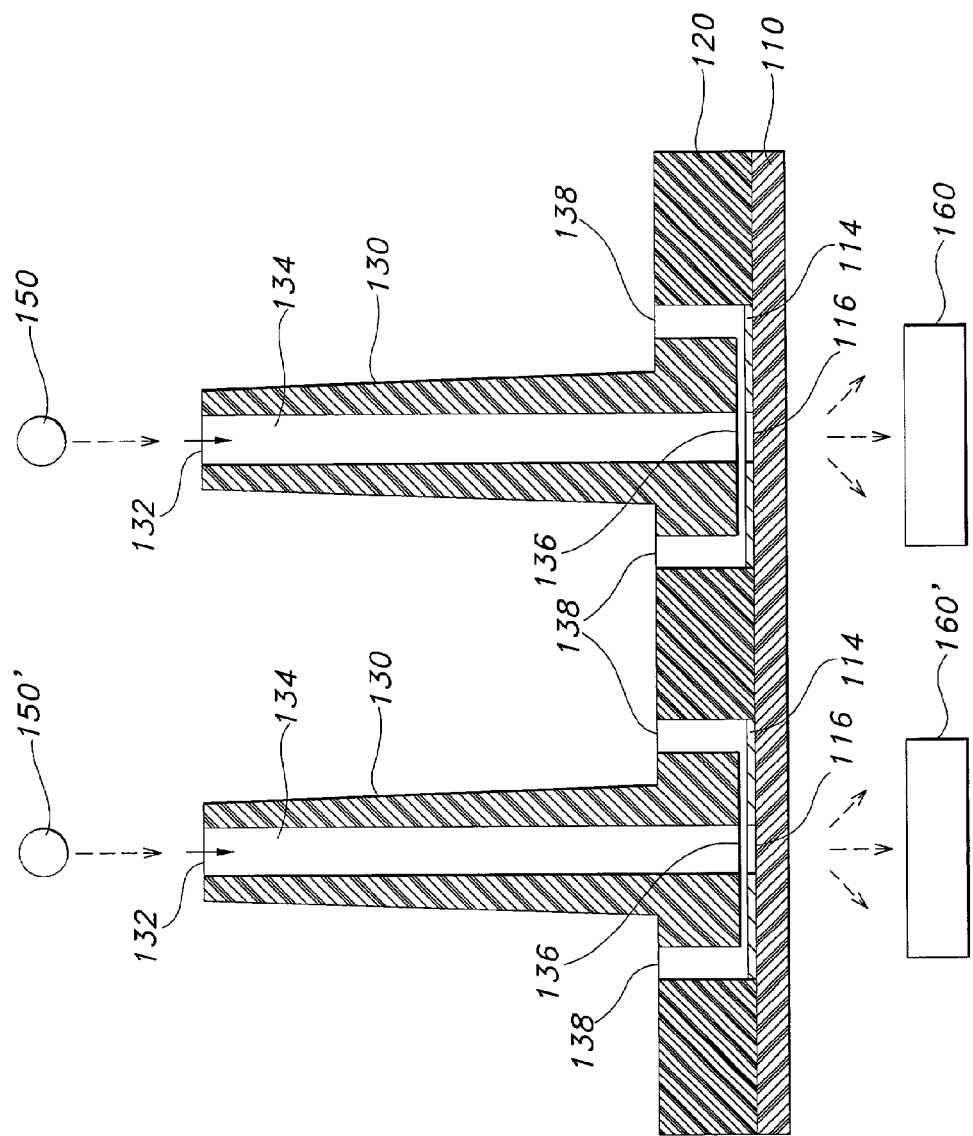

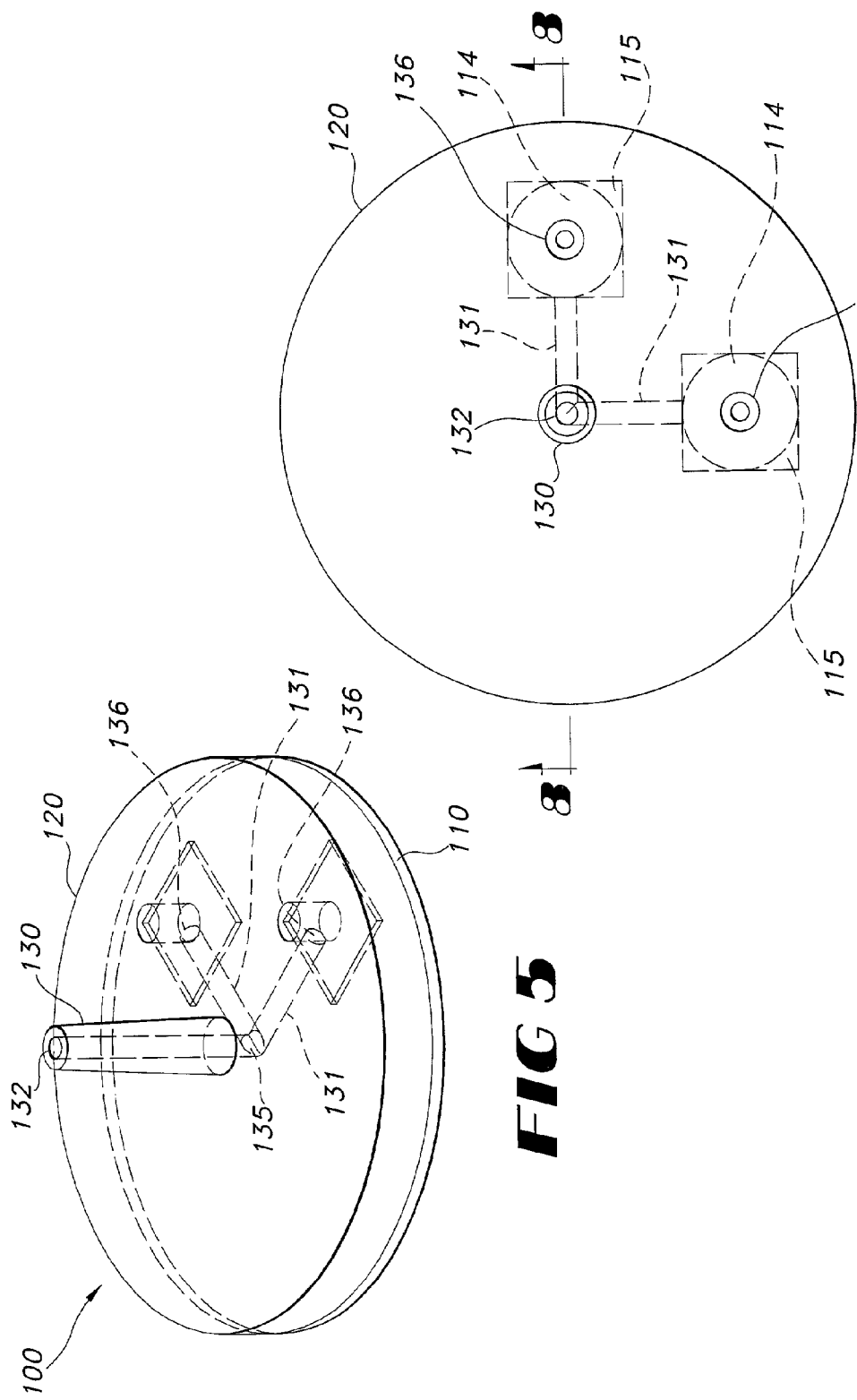

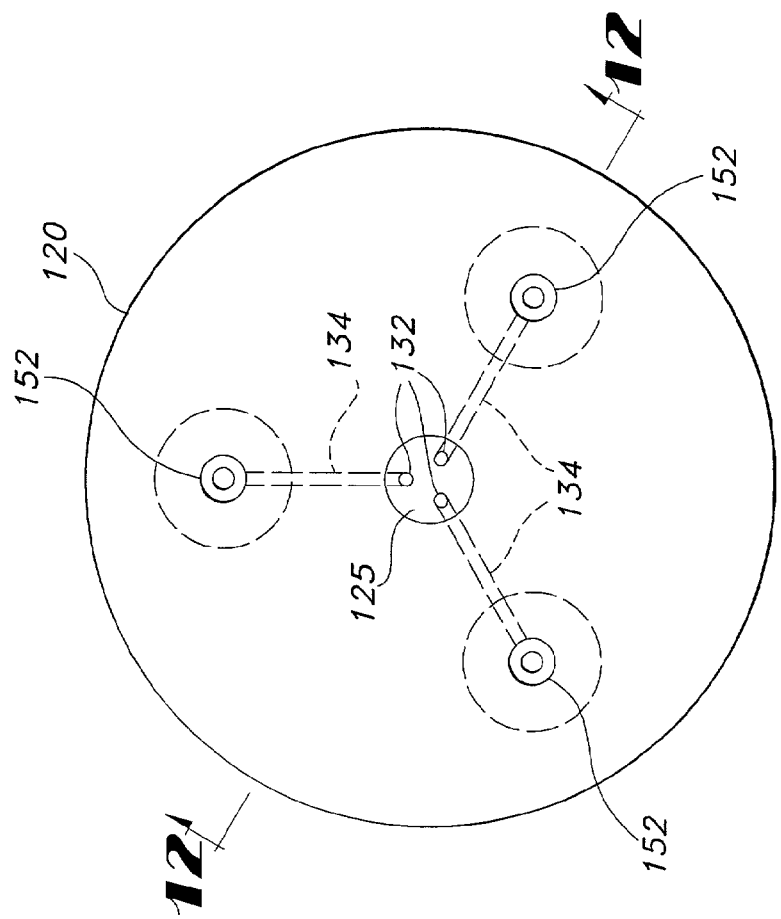
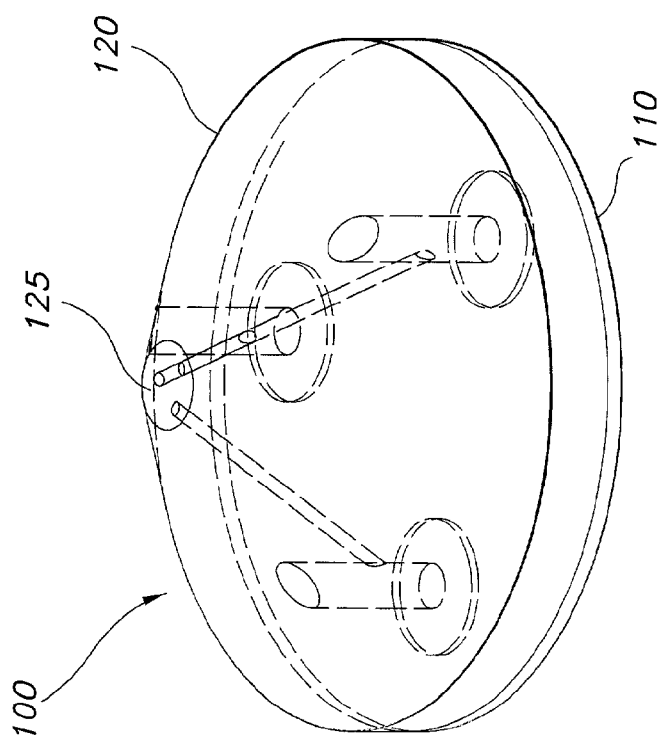
FIG 11
FIG 9

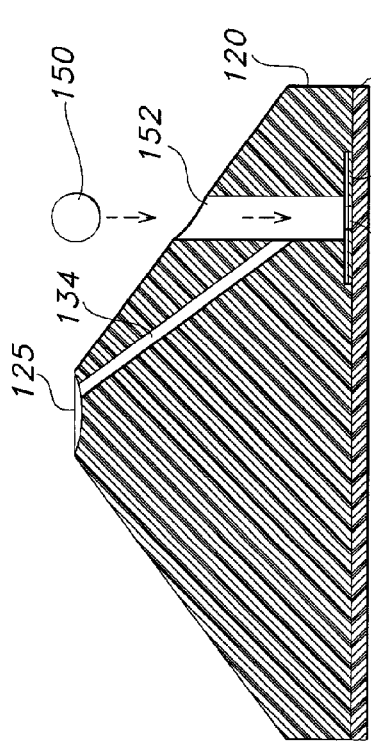
FIG 12
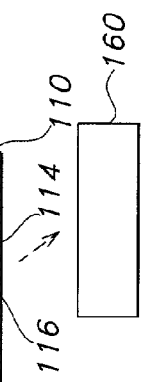
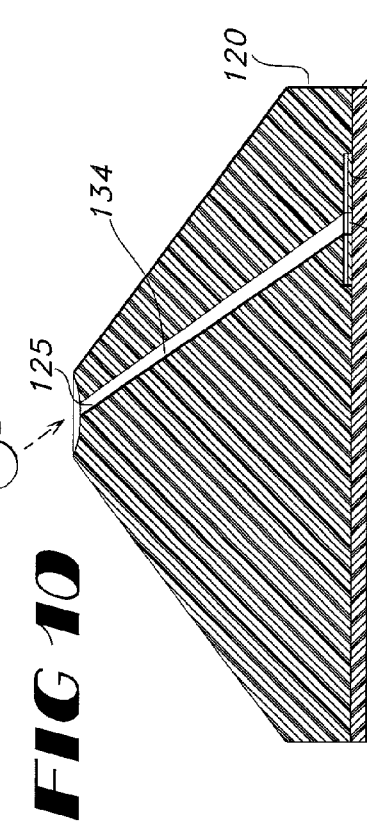
FIG 12A
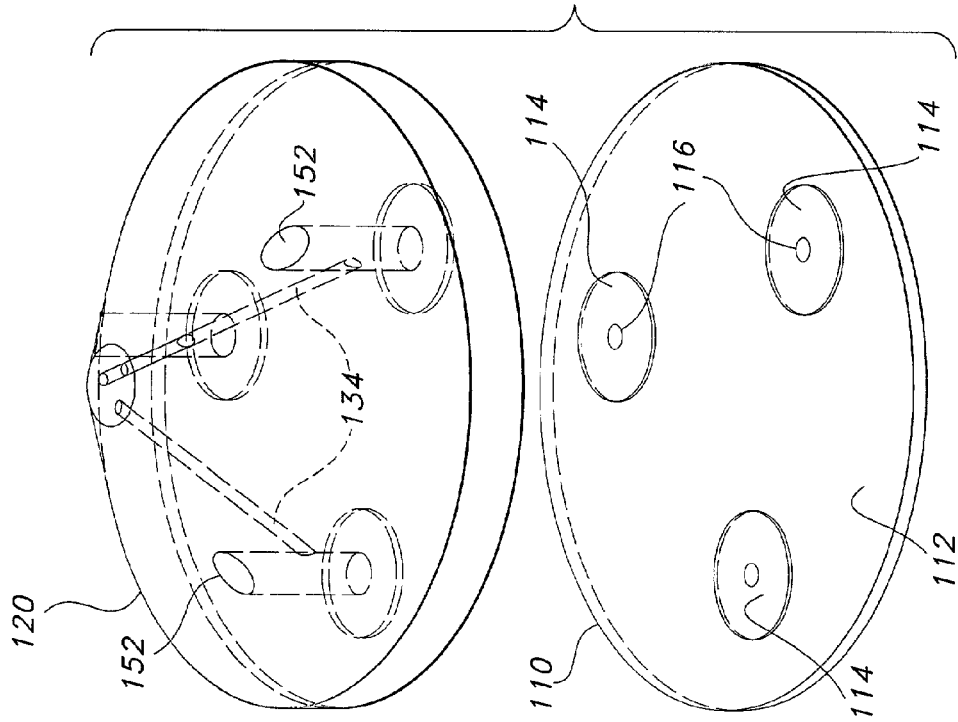
FIG 10

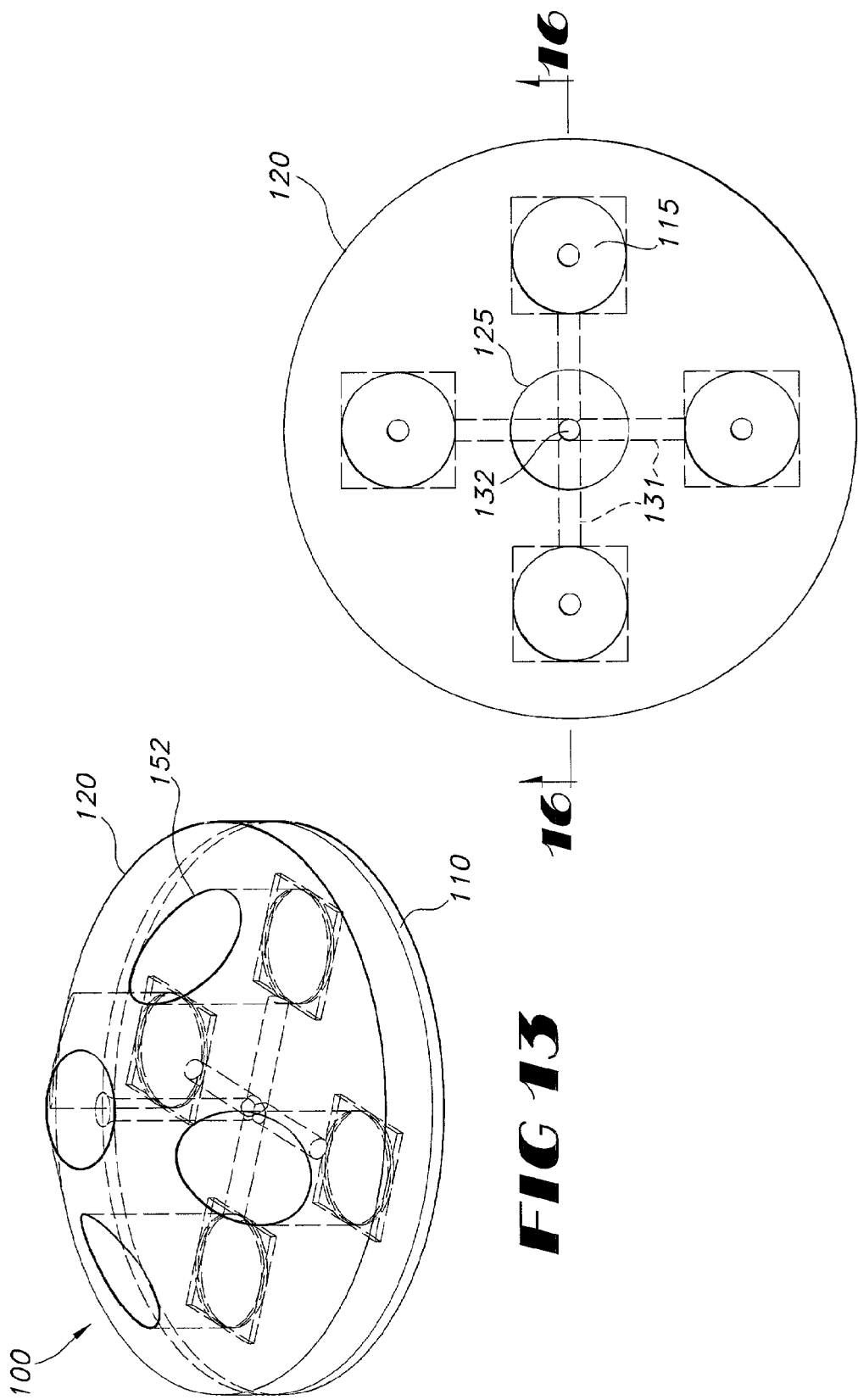

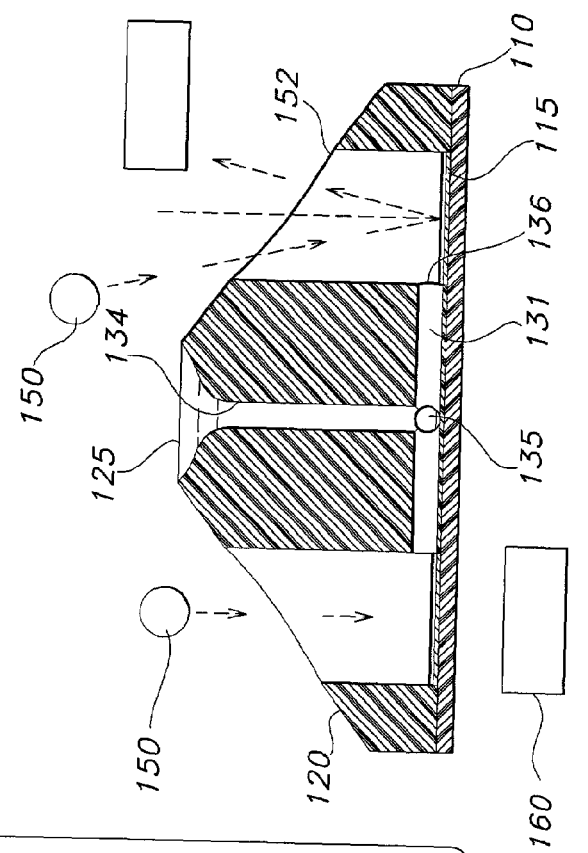
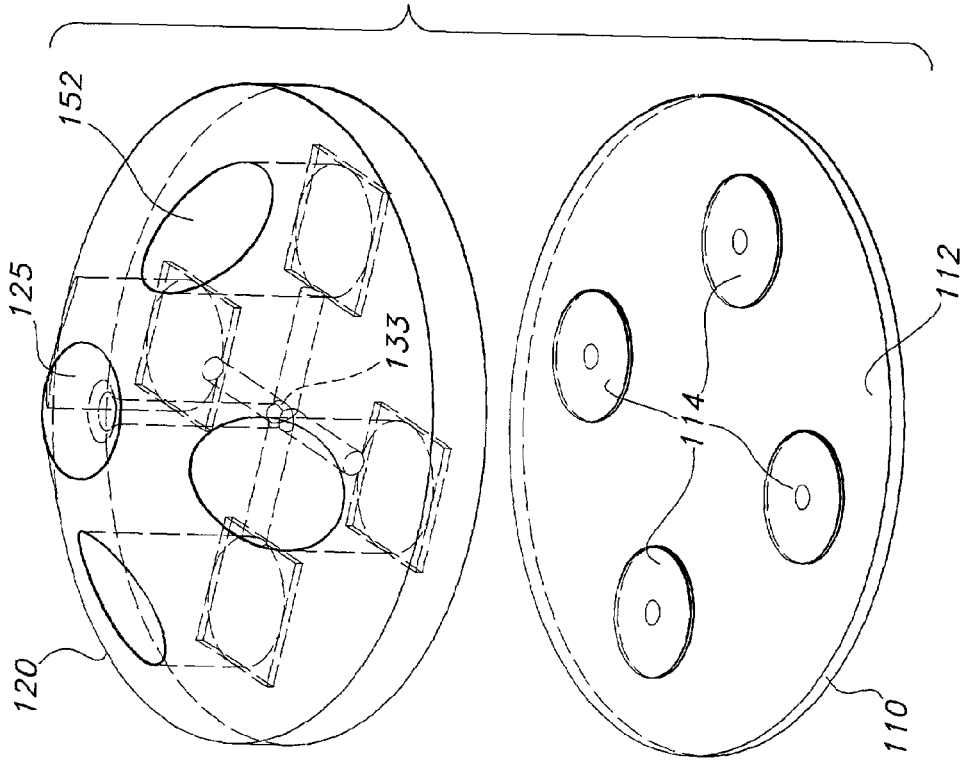

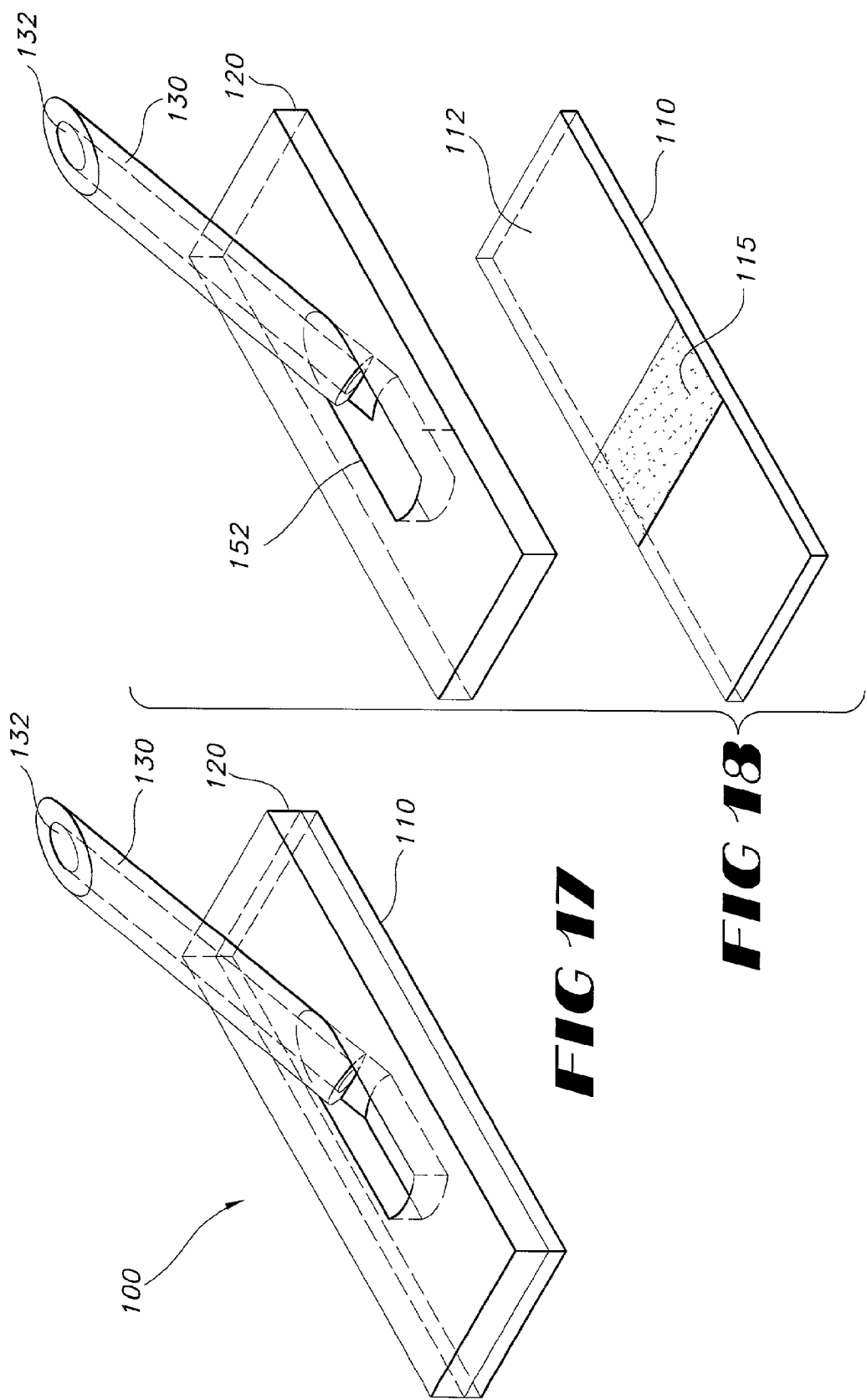

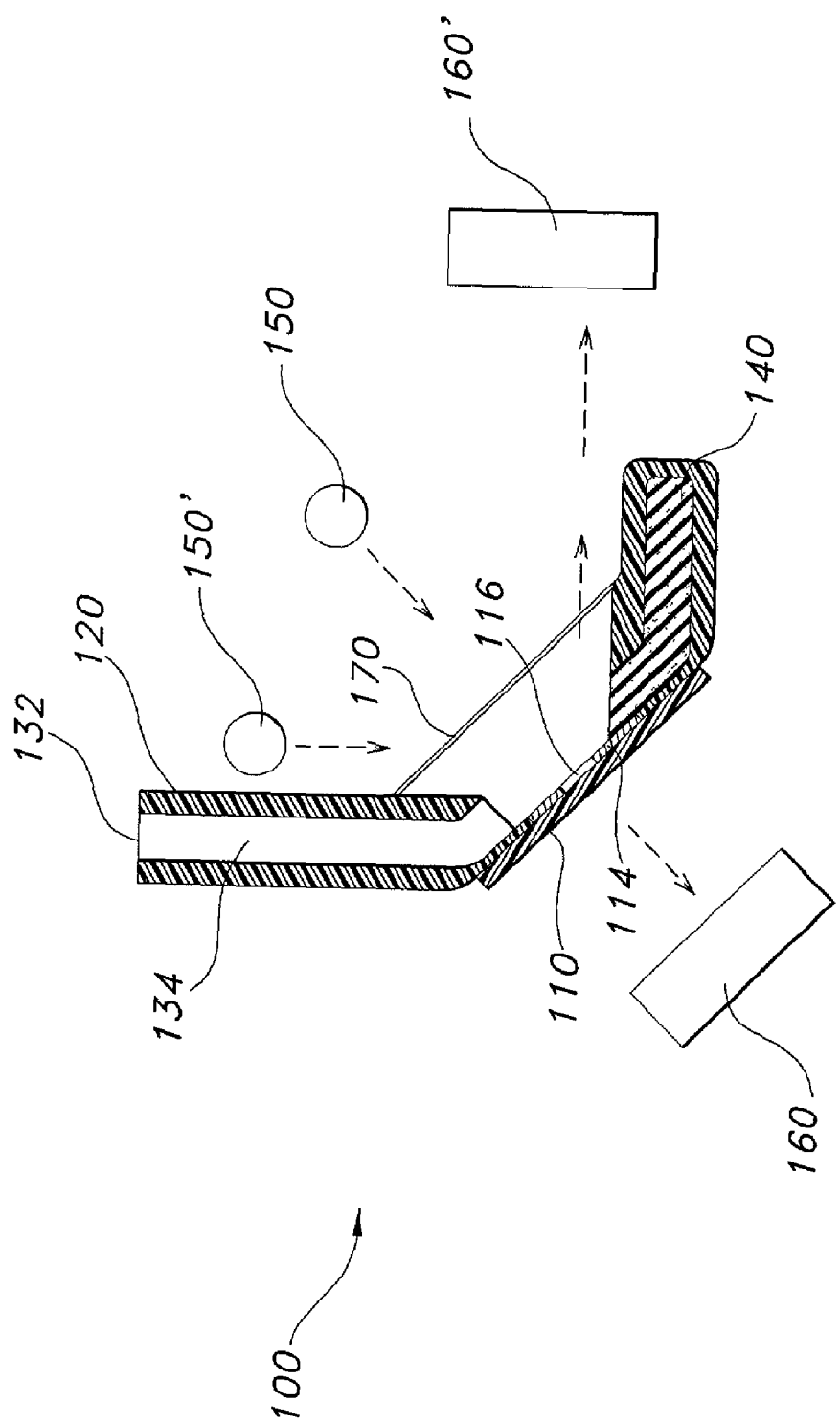

DIAGNOSTIC DEVICE AND SYSTEM

FIELD OF THE INVENTION

The present invention relates to diagnostic devices. Particularly, the present invention relates to diagnostic devices that incorporate a means for directing a sample to a test surface.

BACKGROUND

The present invention relates to diagnostic devices that can be used to detect analytes present in a medium. The devices comprise a surface upon which is printed in a pattern a binder. Upon attachment of analyte to the binder that is printed in a pattern on the surface, diffraction of light that is transmitted through or reflected off of the printed surface via the physical dimensions and defined placement of the binder.

U.S. Pat. No. 4,992,385 to Godfrey, et al. describes a method of preparing a diffraction grating from a thin polymer film for subsequent use as a sensing device. The sensing device described in 4,992,385 requires the use of a spectrophotometric technique to detect changes in the device's optical properties due to analyte binding. The device and method described in 4,992,385 require a complex detection method to detect changes in the diffraction pattern because changes in a diffraction pattern are more subtle than the qualitative determination that is made to determine whether a diffraction image is formed or is not formed.

U.S. Pat. No. 5,196,350 to Backman et al. describes an optical detection method for detecting the presence of specific ligands. The method described in 5,196,350 is an optical detection method for detecting specific ligands that requires a mask comprising slits to produce a diffraction pattern. An immunoassay device is placed between the mask and light source, so that binding by an analyte causes a change in the diffraction or interference pattern caused by the mask. Again, this method also requires a complex detection method to detect changes in a diffraction pattern and confirm the presence of a ligand.

International Publication No. WO 94/13835 describes a method and a system to detect biological macromolecules via diffraction of light from a probe of predetermined dimensions that diffracts light in a known pattern. The probe comprises an active surface that is able to highly concentrate the macromolecules relative to their concentration in the sample solution. The method and the system described in WO 94/13835 also require the use of a complex detector and an analyzer in order to detect changes in the diffraction pattern produced by the probe.

The methods, systems and devices discussed above do not provide a means for directing a sample to a test surface. What is needed is a simple, easy to use method, system and device for detecting an analyte that provides a means for directing a sample to a test surface.

SUMMARY OF THE INVENTION

In contrast to the methods and systems discussed above, researchers at the present company have developed methods, systems and devices that are capable of detecting the presence of an analyte simply by detecting the formation of a diffraction pattern or image due to binding of an analyte in a sample. Therefore, the appearance of a diffraction image is used to confirm the presence of analyte in a sample. In many of the embodiments, the diagnostic devices do not diffract light before exposure to analyte and do diffract light after exposure to analyte. Thus, the devices, systems and methods do not require complex apparatus or analyzers to measure changes in the diffraction pattern or to provide a result.

The present invention provides a device for detecting the presence of an analyte in a sample. In one embodiment, the device includes a substrate, a binder printed in a defined pattern onto a surface of the substrate, and a guide that directs a sample towards the surface of the substrate that is printed with the binder. In one embodiment, the guide is designed to permit light or other electromagnetic radiation to be directed through the guide to the surface of the substrate printed with the binder. In another embodiment, the device also includes an additional opening or window to permit light or other electromagnetic radiation to be directed through the opening to the surface of the substrate printed with the binder. Devices of the present invention may also further include an optional layer of wicking agent on the surface of the substrate printed with the binder. If a layer of wicking agent is included in the devices, it is desirable that the layer of wicking agent includes an opening through which light or other electromagnetic radiation can be directed to the surface of the substrate printed with the binder so that the surface can be tested for analyte binding.

In yet another embodiment that provides for multiple test loci, the devices of present invention comprise a guide that directs at least a first portion of a sample toward a first location and directs at least a second portion of the sample to a second location. The binder printed on the second location may be the same as or different from the binder than the binder printed on the first location. The first and second locations may be on the same film or surface or on different films or surfaces.

The present invention provides a means for directing a sample towards the surface of a diffraction-based diagnostic device in which a substrate that is printed with an analyte-specific binder. Exemplary means for directing a sample towards the surface may include, but are not limited to, one or more of any of the following: capillaries, conduits, tubular structures, channels, slots, parallel plates, grooves and other types of openings, passages or penetrations, porous materials of various shapes and configurations, surfaces having varying degrees of surface energy or hydrophobicity, pumps, vacuums, suction, air pressure, electrostatic attraction or repulsion, hydrophobic or hydrophilic interaction, electromagnetic coercion, osmotic pressure, centripetal acceleration, localized heating or cooling, charged gas bladders and so forth.

In at least one embodiment, the means for directing is a structure that directs the sample from a source for the sample toward the surface of that is printed with a binder through use of capillary forces or capillary action. Desirably, the means for directing a sample from a source of the sample toward a surface of the substrate that is printed with a binder comprises a material or a structure that has an affinity for the sample that is greater than the affinity of the sample to the source from which the sample is obtained.

The present invention also provides a system for detecting the presence of an analyte in a sample. The system comprises a substrate, a binder printed in a pattern onto a surface of the substrate, and a means for directing a sample towards the surface of the substrate printed with the binder; and a light or other electromagnetic radiation source that is positioned and aligned so that the light or other electromagnetic radiation source can be directed through the means for directing a sample to the surface of the substrate printed with the binder or through a second opening provide on the device so that the light or other electromagnetic radiation source can be directed through the second opening to the surface of the substrate printed with the binder. A system of the present invention may also further include a means for detecting a diffraction signal, image or pattern. The light source or other electromagnetic radiation may be transmitted through or reflected from the surface of the substrate printed with the binder to detect diffraction. If light is to be transmitted through the surface of a film to detect diffraction, it is desirable that the film is transparent or at least partially transparent to the light that will be used to detect diffraction. If light is to be reflected off of a surface to detect diffraction, it is desirable that the surface reflects as much of the light as possible.

In a desirable embodiment, the present invention provides a disposable, diffraction-based diagnostic device for detecting the presence of at least two analytes in a sample. The disposable, diffraction-based device comprises a film, a first binder for a first analyte printed in a pattern onto at least a first portion of the surface of the film, a first means for directing at least a portion of a sample from a source of the sample towards the at least first portion of the printed surface of the film, a second binder for a second analyte printed in a pattern onto at least a first portion of the surface of the film, and a second means for directing at least a portion of a sample from a source of the sample towards the at least second portion of the printed surface of the film.

Features, aspects and advantages of the present invention will become better understood with reference to the following description and the appended claims. The accompanying drawings, which are incorporated in and constitute a part of this specification, illustrate several examples of the invention and, together with the description, serve to explain the principles of this invention.

BRIEF DESCRIPTION OF THE FIGURES

The invention is hereinafter more particularly described by way of examples with reference to the following drawings in which:

FIGS. 1 and 1A are perspective views of a first diagnostic device and a second illustrated diagnostic device, respectively.

FIGS. 2 and 2A are exploded, perspective views of the first and the second diagnostic devices.

FIGS. 3 and 3A are plan views of the first and the second diagnostic devices.

FIGS. 4 and 4A are cross-sectional views of the first and the second diagnostic devices taken along line 4 of FIGS. 3 and 3A, respectively.

FIG. 5 is perspective a view of a third illustrated diagnostic device.

FIG. 7 is a plan view of the third diagnostic device.

FIG. 9 is a perspective view of a fourth illustrated diagnostic device.

FIG. 10 is an exploded, perspective view of the fourth diagnostic device.

FIG. 11 is a plan view of the fourth diagnostic device.

FIG. 12 is a cross-sectional view of a fourth diagnostic device taken along line 12 of FIG. 11.

FIG. 12A is cross-sectional view of an alternate device that is a modification of the device illustrated in FIGS. 9-12.

FIG. 13 is perspective a view of a fifth illustrated diagnostic device.

FIG. 14 is an exploded, perspective view of the fifth diagnostic device.

FIG. 15 is a plan view of the fifth diagnostic device.

FIG. 16 is a cross-sectional view of the fifth diagnostic device taken along line 16 of FIG. 15.

FIG. 17 is a perspective view of an sixth illustrated diagnostic device.

FIG. 18 is an exploded, perspective view of the sixth diagnostic device.

FIG. 21 is a cross-sectional view of a seventh illustrated diagnostic device.

Figure 1:
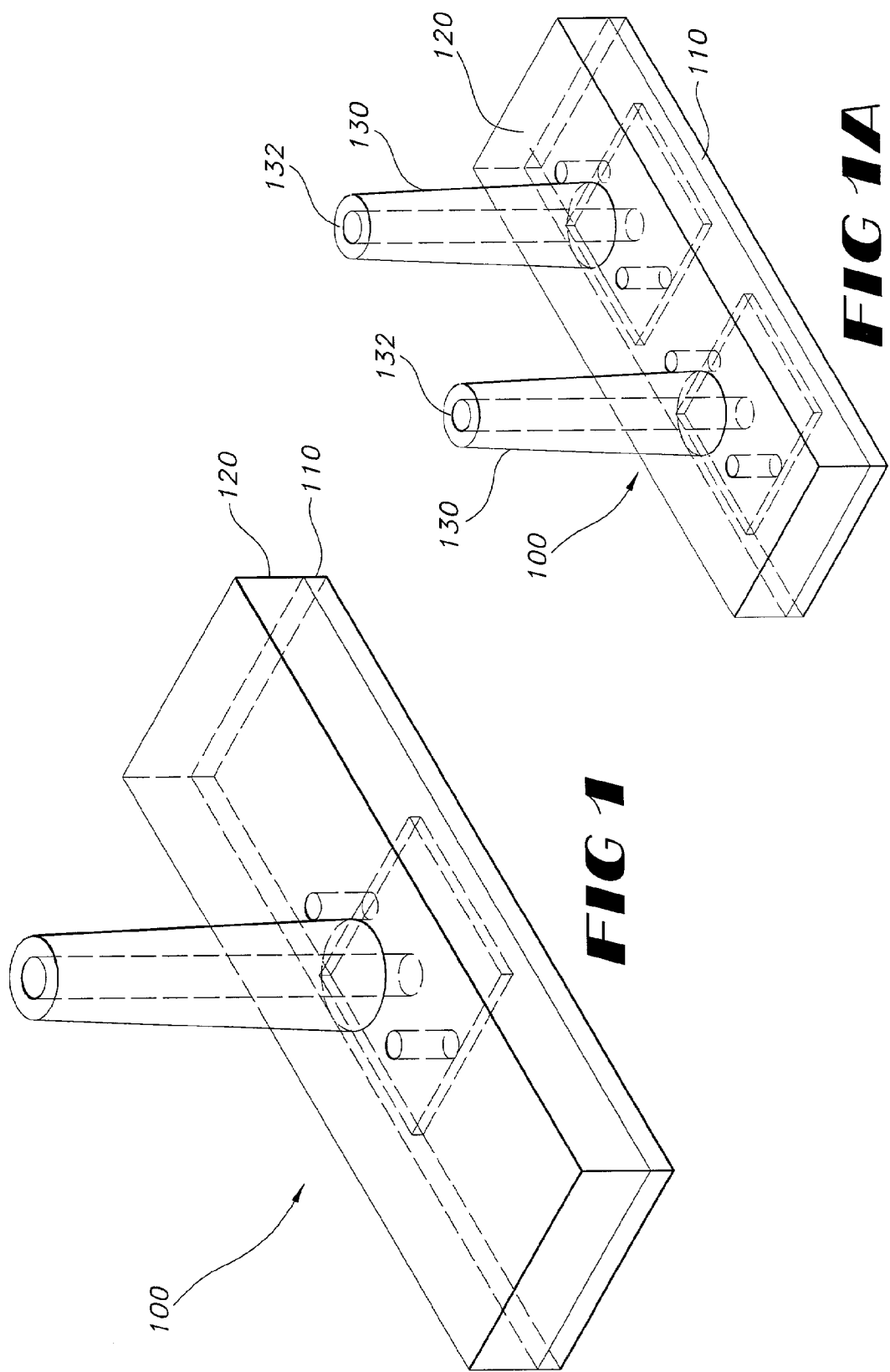

Repeated use of reference characters in the present application and drawings is intended to represent the same, similar or analogous features or elements of the invention.

DETAILED DESCRIPTION

Although the present invention is described in the context of several specific examples, configurations and embodiments, it will be appreciated that further combinations or alterations of the examples, configurations and embodiments illustrated herein and described herein may be made by one skilled in the art without departing from the spirit and scope of the present invention. In addition, although reference is often made with respect to diffraction-based diagnostic devices, methods and systems for detecting a protein, those skilled in the art will appreciate that other modifications may be made to adapt the diagnostic devices, methods and systems for use with non-diffraction based diagnostic devices, methods and systems and for detecting analytes other than proteins. In the following discussion, reference is made to several figures to illustrate a few specific examples and embodiments of the present invention.

The present invention provides diagnostic devices, systems and methods that include a fluidic guide or other means for directing a sample to a test surface. Desirably, the fluidic guide or means for directing a sample to a test surface is connected to the test surface to form a unified device or structure. Desirably, the means for directing a sample to a test surface is in direct fluid communication with the test surface. Such means facilitate the use of such devices, systems and methods by individuals and can be used to provide an improved format for using diffraction-based diagnostic devices, system and methods. Generally, a means for directing a sample to a test surface may be any means, device or structure that may be used to urge, force, compel or otherwise facilitate the transport of a fluid sample from one location to another. As used herein, a "fluid" includes a liquid, a gas, mixtures of gasses and/or liquids, solutions, emulsions and/or suspensions and may comprise undissolved particles or other solids and may further include homogeneous or heterogeneous mixtures comprising at least one fluid.

Methods of detecting analytes and systems and devices that detect analytes via the formation of a diffraction image are disclosed and described in the U.S. patents and International PCT applications discussed herein. Methods, systems and devices that detect the presence of an analyte by detecting the formation, i.e. the presence, of a diffraction pattern rather than detecting changes within a diffraction image provide a less complex method for determining the presence of an analyte.

Examples of methods, systems and devices for detecting an analyte via the formation of a diffraction image are disclosed and described in U.S. Pat. No. 5,922,550, U.S. Pat. No. 6,020,047, U.S. Pat. No. 6,221,579 and International Publication No. WO 98/27417 which are hereby incorporated by reference herein in their entirety. The devices described in the above-referenced documents can be produced by printing a species onto a surface. The species is selected to bind, react or otherwise associate with an analyte of interest and is referred to herein as a "binder". A binder may include any chemical species, compound, composition, moiety, particle and so forth that will bind, react or otherwise associate with the analyte of interest. Preferably, the binder is specific to the analyte of interest or a class of analytes of interest and does not appreciably bind, react or otherwise associate with any other matter that may be found in the sample of interest. The binder can be any analyte-specific receptor material that can be printed onto a substrate and that will specifically bind to an analyte of interest.

Thus, the binder is one part of a specific binding pair and includes, but is not limited to, antigen/antibody, enzyme/substrate, oligonucleotide/DNA, chelator/metal, enzyme/inhibitor, bacteria/receptor, virus/receptor, hormone/receptor, DNA/RNA, or RNA/RNA, oligonucleotide/RNA, and binding of these species to any other species, as well as the interaction of these species with inorganic species. The binder material that is printed onto the substrate is characterized by an ability to specifically bind the analyte or analytes of interest. The variety of materials that can be used as a binder material are limited only by the types of material which will combine selectively (with respect to any chosen sample) with the analyte. Sub-classes of materials which can be included in the overall class of receptor materials includes toxins, antibodies, antigens, hormone receptors, parasites, cells, haptens, metabolites, allergens, nucleic acids, nuclear materials, autoantibodies, blood proteins, cellular debris, enzymes, tissue proteins, enzyme substrates, coenzymes, neuron transmitters, viruses, viral particles, microorganisms, proteins, polysaccharides, chelators, drugs, and any other member of a specific binding pair. This list only incorporates some of the many different materials that can be printed onto the substrate to produce a diagnostic device. Whatever the selected analyte of interest is, the binder is designed to bind, react or otherwise associate with the analyte(s) of interest.

Generally, the binder is printed onto a substrate, for example a plastic film, in a defined pattern such that the binder-printed film does not diffract electromagnetic radiation when the electromagnetic radiation is reflected off of or transmitted through the binder-printed film but diffracts electromagnetic radiation after the binder-printed film is exposed to the analyte and the analyte has bound, reacted or otherwise associated with the binder. Alternatively, the binder-printed film or surface may exhibit a measurable increase or decrease in diffraction after exposure to the analyte. For example, a film may be printed with a binder such that the binder-printed film does not diffract light but does diffract after an analyte binds, associates or otherwise reacts with the binder-printed surface. In another example, the binder-printed film initially diffracts light but does not diffract light or diffracts less after an analyte binds, associates or otherwise reacts with the binder-printed surface. In yet another example, the film may be printed with a binder so that binder-printed film initially diffracts light but when the analyte binds with binder-printed surface, light is diffracted to a measurably greater extent. Thus, the presence of analyte can be determined by a measurable change in diffraction of light that is transmitted through or reflected off of the substrate surface. If light or other electromagnetic radiation is to be transmitted through the surface of a film to detect diffraction, it is desirable that the film is transparent or at least partially transparent to the light or other electromagnetic radiation that will be used to detect diffraction.

Devices of the present invention include a surface or at least a portion of a surface that is printed with a binder. The printing of the surface may be accomplished by microcontact printing the binder onto the surface in a defined pattern. Microcontact printing is desirable and allows printing of patterns with size features of about 100 μm and smaller. Features in this size range are desirable for diffraction when the electromagnetic radiation wavelength is in the spectrum of visible light, that is from about 4000 Angstroms to 7700 Angstroms. However, it is noted that light over other wavelengths, both longer and shorter wavelength electromagnetic radiation may be used to detect diffraction. A pattern of binder allows for the controlled attachment of analyte or analyte receptor. An elastomeric stamp may be used to transfer binder "ink" to the surface. If the stamp is patterned, a patterned binder layer will be printed on the surface when the stamp is wet with the binder and then contacted with the surface.

Gold-coated, printed films that produce diffraction patterns and methods of contact printing such films are described and disclosed in U.S. Pat. No. 6,202,047 and U.S. Pat. No. 6,048,623 which are hereby incorporated by reference herein in its entirety. U.S. Pat. Nos. 6,202,047 and 6,048,623 describe methods of microcontact printing self-assembling monolayers that allow for the selective placement of reagents that can react chemically or physically with an analyte or a group of analytes that are of interest to produce a diffraction image.

Generally, an analyte may be any stimulus including but not limited to any chemical or biological species, compound, composition, moiety, particle, and so forth that will bind, react or otherwise associate with the binder or with which the binder will respond. Analytes that are contemplated as being detected include, but are not limited to, one or more the following: species of bacteria, including, but not limited to, *Neisseria meningitides* cerogroups A, B, C, Y and W135, *Streptococcus pneumoniae, E. coli* K1; yeasts, fungi; viruses including, but not limited to, *Haemophilus influenza* type B or RSV; rheumatoid factors; antibodies including, but not limited to, IgG, IgM, IgA and IgE antibodies; antigens including, but not limited to, carcinoembryonic antigen, streptococcus Group A antigen, streptococcus Group B antigen, viral antigens, an antigen derived from microorganisms, antigens associated with an autoimmune disease, tumors; allergens; enzymes; hormones; polysaccharides; proteins; lipids; carbohydrates; drugs including, but not limited to, drugs of abuse and therapeutic drugs, nucleic acids; haptens, environmental agents other blood-born disease markers; and so forth.

A binder may be microprinted on a polymer film or other substrate. Desirably, a binder is selected and printed that is an analyte-specific receptor material and specifically binds to the analyte or class of analytes of interest. Thus, the binder material and analyte are defined as a specific binding pair and includes, but is not limited to, antigen/antibody, enzyme/substrate, oligonucleotide/DNA, chelator/metal, enzyme/inhibitor, bacteria/receptor, virus/receptor, hormone/receptor, DNA/RNA, or RNA/RNA, oligonucleotide/RNA, and binding of these species to any other species, as well as the interaction of these species with inorganic species. The binder material that is printed on to a substrate layer is characterized by an ability to specifically bind the analyte or analytes of interest. The variety of materials that can be used as a binder material are limited only by the types of material which will combine selectively (with respect to any chosen sample) with the analyte. Subclasses of materials which can be included in the overall class of binder materials include toxins, antibodies, antigens, hormone receptors, parasites, cells, haptens, metabolites, allergens, nucleic acids, nuclear materials, autoantibodies, blood proteins, cellular debris, enzymes, tissue proteins, enzyme substrates, coenzymes, neuron transmitters, viruses, viral particles, microorganisms, proteins, polysaccharides, chelators, drugs, and any other member of a specific binding pair.

For example, if the target analyte is a protein, an antibody that is specific to the protein may be used as a binder. Antibodies can be purchased from a variety of suppliers. A listing of suppliers and a listing of antibodies that are commercially available are provided in Linscott's Directory (1998) pp. 1-207. Examples of pairings of specific binders and specific analytes or specific classes of analytes that can be detected via the use of a specific binder are known and are known to persons skilled in the art and can be obtained from various sources including Linscott's Directory which is hereby incorporated by reference.

The methods, systems and devices discussed herein provide a test for detecting an analyte or a class of analytes and may be used, for example to detect for contamination by microorganisms or other types of chemical or biological contamination. Such devices, systems and methods have particular use in health diagnostic applications such as diagnostic kits for the detection of antigens or antibodies associated with specific medical conditions, microorganisms, and blood constituents. Analytes may be detected in a variety of sample media including, but not limited to, blood, urine, menses, vaginal secretions, nasal secretions, saliva and so forth. If the sample media is not fluid, it may be desirable to dissolve the sample in a fluid.

U.S. Pat. No. 6,180,288 and International Publication No. WO 98/43086 disclose and describe the use of one or more responsive gels coated on a patterned self-assembling monolayer and the use of such devices. The responsive gels described therein react or respond to a stimulus, i.e. an analyte, to produce a diffraction image. U.S. Pat. No. 6,180, 288 and International Publication No. WO 98/43086 are both hereby incorporated by reference herein in their entirety.

Diffraction-based detectors and methods of detection using optical diffraction that do not require self-assembled monolayers are disclosed and described in U.S. Pat. No. 6,060,256 and International Publication No. WO 99/31486. U.S. Pat. No. 6,060,256 and International Publication No. WO 99/31486 are hereby incorporated by reference herein in their entirety. U.S. Pat. No. 6,060,256 and International Publication No. WO 99/31486 also disclose and describe the optional addition of nutrients for a specific class of microorganisms with such diagnostic devices, systems and methods to provide for the detection of lower concentrations of analytes.

U.S. Pat. No. 6,221,579 and International Publication No. WO 00/34781 disclose and describe the addition of diffraction enhancing elements. Diffraction enhancing element particles that may be used with the present invention include, but are not limited to, glass, cellulose, synthetic polymers or plastics, latex, polystyrene, polycarbonate, bacterial or fungal cells and so forth. A desirable particle size ranges from a diameter of approximately 0.1 µm to 100.0 µm. The composition of the element particle and structural and spatial configuration of the particle is not critical to the present invention. However, it is desirable that the difference in refractive index between the medium and the enhancing element is between 0.1 and 1.0. Diffraction enhancing elements are optionally included in such devices, systems and methods to provide for the detection of smaller species of analyte, such as DNA, RNA other low molecular weight analytes and low molecular weight surface markers on organisms. U.S. Pat. No. 6,221,579 and International Publication No. WO 00/34781 describe the modification of microspheres so that the microspheres are capable of binding with a target analyte and to the device surface. The microspheres are capable of producing a substantial change in height or refractive index to enhance diffraction, thereby increasing the efficiency of such devices, systems and methods and can provide for the detection of smaller species of analyte. U.S. Pat. No. 6,221,579 and International Publication No. WO 00/34781 are hereby incorporated by reference herein in their entirety.

International Publication No. WO 00/36416 describes and discloses devices and systems comprising a patterned deposition of antibody-binding proteins for detecting antibodies. International Publication No. WO 00/136416 is also hereby incorporated by reference herein in its entirety.

Accordingly, there is a need to provide diagnostic methods, devices and systems that are easy to use by professional and nonprofessionals alike by providing devices and systems that comprise a means for directing a sample to a test surface of a diagnostic device. Methods, devices and systems of the present invention provide a means for directing a sample to a test surface of a diagnostic device that forms an integral component of a diagnostic device. Advantageously, these methods, systems and devices may used by individuals at home to monitor health-related conditions. It is also desirable to provide a means for directing a sample to a test surface that optionally directs portions of the sample to more than one test loci to allow for the detection of more than one analyte or to provide a control test or a back-up test. Such methods, devices and systems are also provided in at least one embodiment of the present invention.

By way of example, a guide or other means for directing a sample to a test surface may be used to facilitate the transport of a blood sample from a freshly lanced finger or other body site to a binder-printed diagnostic test surface such as the binder-printed test surfaces disclosed and described in the previously incorporated patents and international publications commonly owned and assigned to the assignee of the present invention. Examples of guides and means for directing a sample to a test surface include, but are not limited to the following: capillaries, conduits, tubular structures, channels, slots, parallel plates, grooves and other types of openings, passages or penetrations, porous materials of various shapes and configurations, surfaces having varying degrees of surface energy or hydrophobicity, pumps, vacuums, suction, air pressure, electrostatic attraction or repulsion, hydrophobic or hydrophilic interaction, electromagnetic coercion, osmotic pressure, centripetal acceleration, localized heating or cooling, charged gas bladders and so forth. The cross-section of the guide or other means may be non-circular. Desirably, the guide or means for directing a sample from a source of the sample towards the surface of the substrate that is printed with a binder directs the sample toward the surface of the substrate that is printed with a binder through use of capillary forces or by capillary action. More desirably, the guide or means comprises a material and a structure that has an affinity for the sample that is greater than the affinity of the sample to the source from which the sample is obtained.

Figure 2:
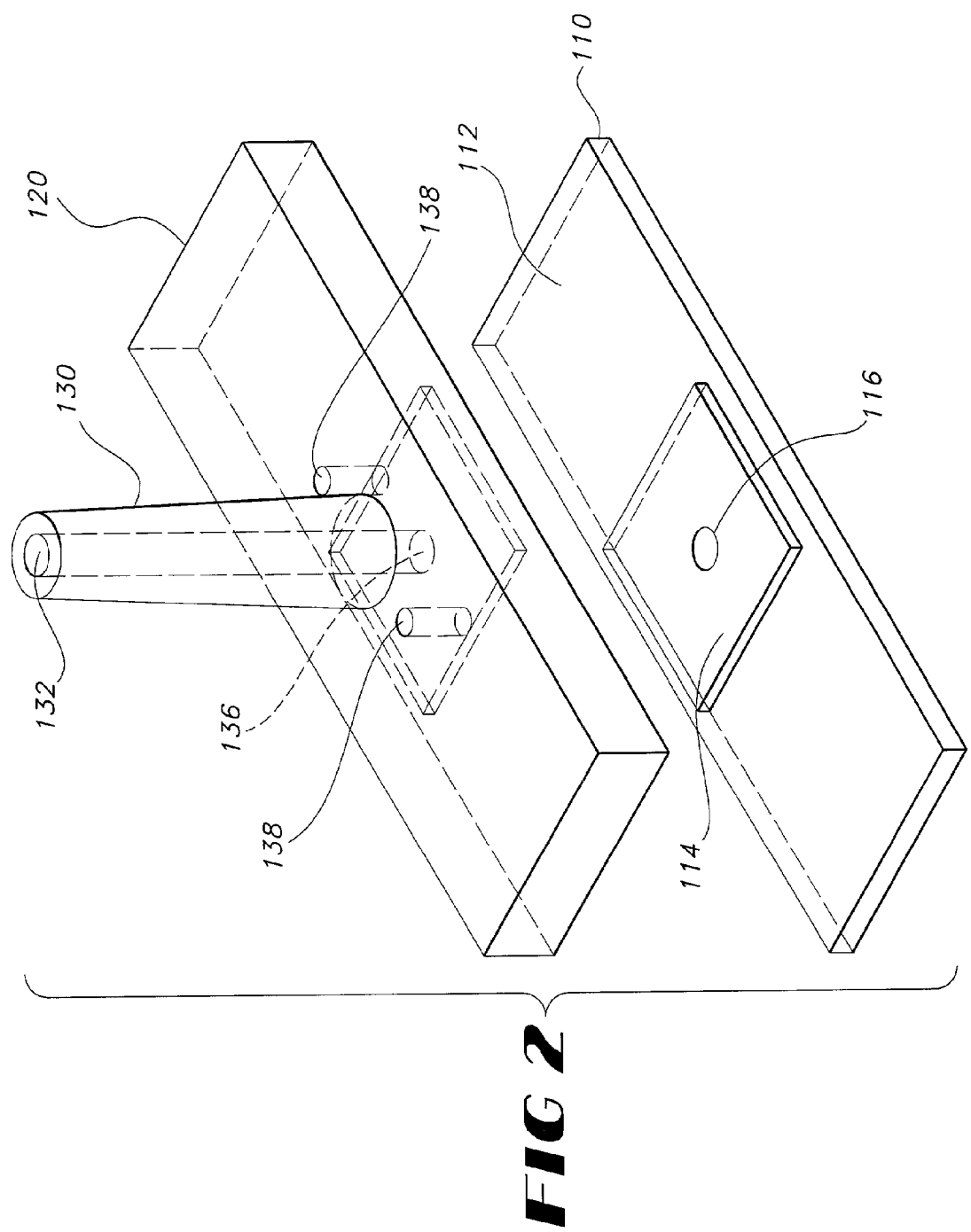
Figure 4:
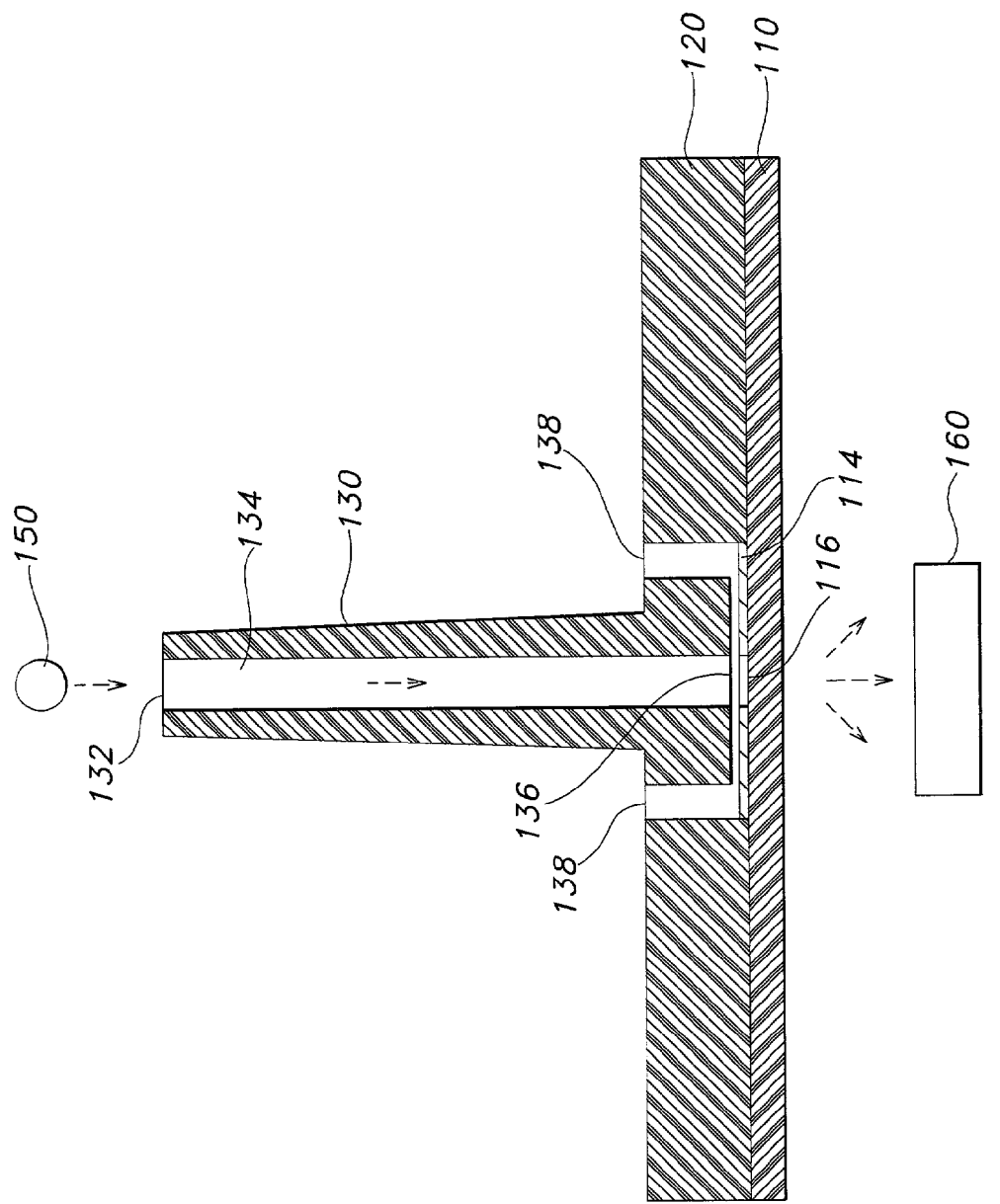

Examples of the present invention that include one or more means for directing a sample to a test surface are illustrated in the accompanying figures and are described in detail herein by reference to the accompanying figures. In the examples illustrated in FIGS. 1-5, the diagnostic device may be a disposable test strip 100 that includes a film 110 that has a surface 112. At least a portion of the surface of the film is printed with a binder for an analyte (not shown). The binder-printed portion of the film is the portion of the film that is exposed to a sample to test for analyte in the sample. The portion of the surface that is printed with a binder may be printed by one of the methods described in the previously discussed patents and international publications that are commonly assigned and discussed above or by an ink-jet printing method. The use of ink-jet printing methods to manufacture diffraction-based diagnostic devices is described and disclosed in U.S. patent application Ser. No. 09/557,453 entitled "Use of Ink-Jet Printing to Produce Diffraction-Based Biosensors" and filed on Apr. 24, 2000. U.S. patent application Ser. No. 09/557,453 entitled "Use of Ink-Jet Printing to Produce Diffraction-Based Biosensors" and filed on Apr. 24, 2000 is hereby incorporated by reference herein in its entirety.

In yet another embodiment, the diagnostic device further includes a wicking agent. The wicking agent may be provided by a layer of wicking material over the binder-printed surface. Desirably, the layer of wicking agent is provided with an opening and the sample is deposited in or direct to the opening. The opening is also useful for transmitting light to the binder-printed surface. The diagnostic devices illustrated in FIGS. 1-4 and 1A-4A, further include an optional layer of wicking agent 114 to facilitate removal of a sample from the portion of the test surface that is printed with the binder after a desired incubation time. Examples of diagnostic devices and test strips that comprise a diffraction-based, diagnostic test locus are disclosed and described in the aforementioned patents and international publications which have incorporated by reference herein. Wicking agents and the use of wicking agents in conjunction with such diagnostic devices and methods are also disclosed and described International Publication No. WO 01/44813. The addition of a wicking agent or a layer of wicking agent in the devices of the present invention is suggested but optional and may improve contact of a sample that is to be tested for an analyte with the binder-printed surface of a diagnostic device, remove unbound diffraction-enhancing elements and/or remove excess sample from the binder-printed surface thus improving the reliability of diagnostic device and methods. Thus, a layer of wicking agent may be incorporated into a diagnostic device or test strip of the present invention to provide desired incubation time of a sample on a binder-printed surface, to remove unbound diffraction-enhancing elements or to eliminate the need to rinse or wash excess sample from the binder-printed surface before testing the surface with light or other electromagnetic radiation. International Publication No. WO 01/44813 is hereby incorporated by reference herein in its entirety. Examples of wicking agents include, but are not limited to polyolefins such as polypropylene, fluoropolymers such as polyvinylidene fluoride, nitrocellulose, cellulose, cellulose acetate, glass microfiber structures and so forth. The wicking agent may be provided as a layer over the binder-printed surface. The layer of wicking agent may be a nonwoven layer, a porous membranes, a semiporous membrane or so forth.

The device generally indicated as 100 includes a means 120 for directing a sample to a test surface. In the example illustrated in FIGS. 1-4, the means 120 for directing a sample to a test surface includes a capillary 130 that is used to direct a liquid sample that is placed near a first opening 132 through an interior passage 134 through the capillary 130 to a second opening 136 that is proximate to a layer of a wicking agent 114. The layer of a wicking agent 114 contacts the portion of the device that is printed with a binder for an analyte and spreads the liquid sample over the binder-printed surface.

In an illustrative example, the device can be used to test blood for an analyte that may be contained in the blood, such as C-reactive protein (CRP). CRP is a biomarker that indicates bacterial infection. An individual may test his or her blood for CRP by first pricking his or her finger and then contacting a blood droplet that is obtained from the pricked portion of the finger to first opening 132. A portion of the blood droplet is then directed from the finger through interior passage 134 to the second opening 136 by capillary action. This brings blood into contact to the test surface 112. The layer of wicking agent 114 then draws the blood sample from second opening 136 and brings blood across the surface of the device that is printed with antibody to CRP which is a binder for CRP. The sample, or at least a portion of the sample, contacts the portion of the device that is printed with the antibody so that CRP that may be contained in the sample is allowed to bind, react or otherwise associate with the antibody that is printed on the surface 112. If CRP is present in the blood sample, the CRP will bind with the binder and any optional diffraction enhancing elements and will diffract light. To detect for the presence of CRP, light is then transmitted through or reflected off of the surface to determine if the surface diffracts light. If the surface diffracts light, the blood sample contains CRP. The means 120 for directing a sample to a test surface may further comprise one or more means for venting pressure 138. Pressure may build up due to the movement of a sample through the means 120 for directing a sample to a test surface and may prevent further movement of the sample through the means 120.

Figure 8:
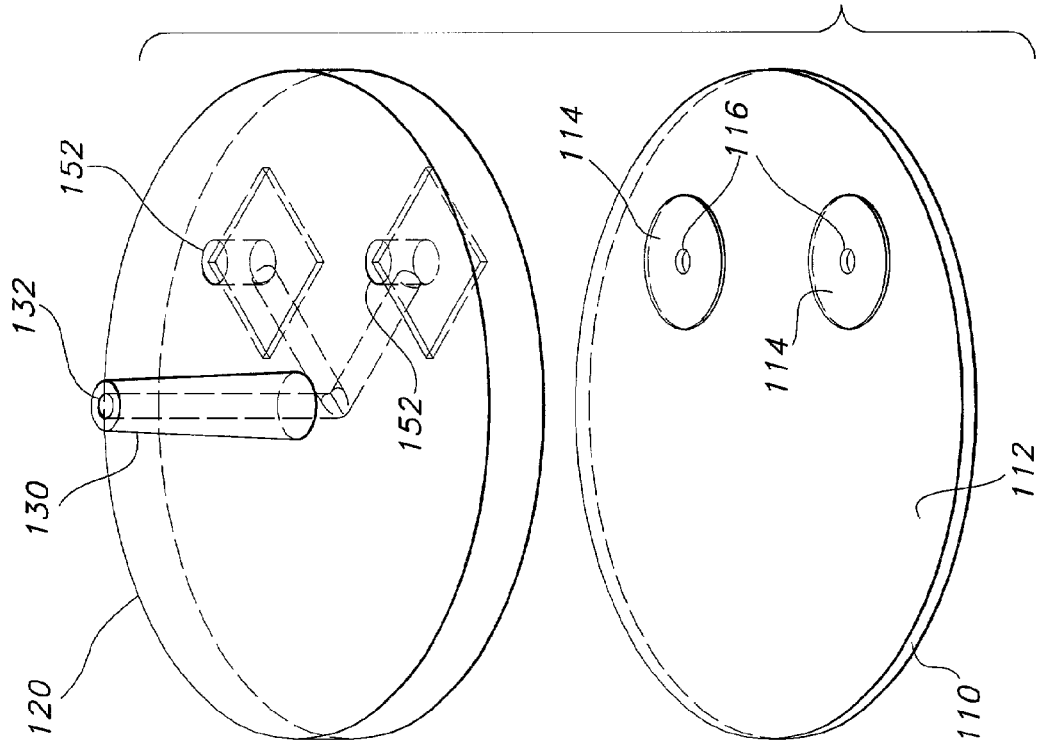
FIG. 8 is a cross-sectional view of the third diagnostic device taken along line 8 of FIG. 7.
Figure 19:
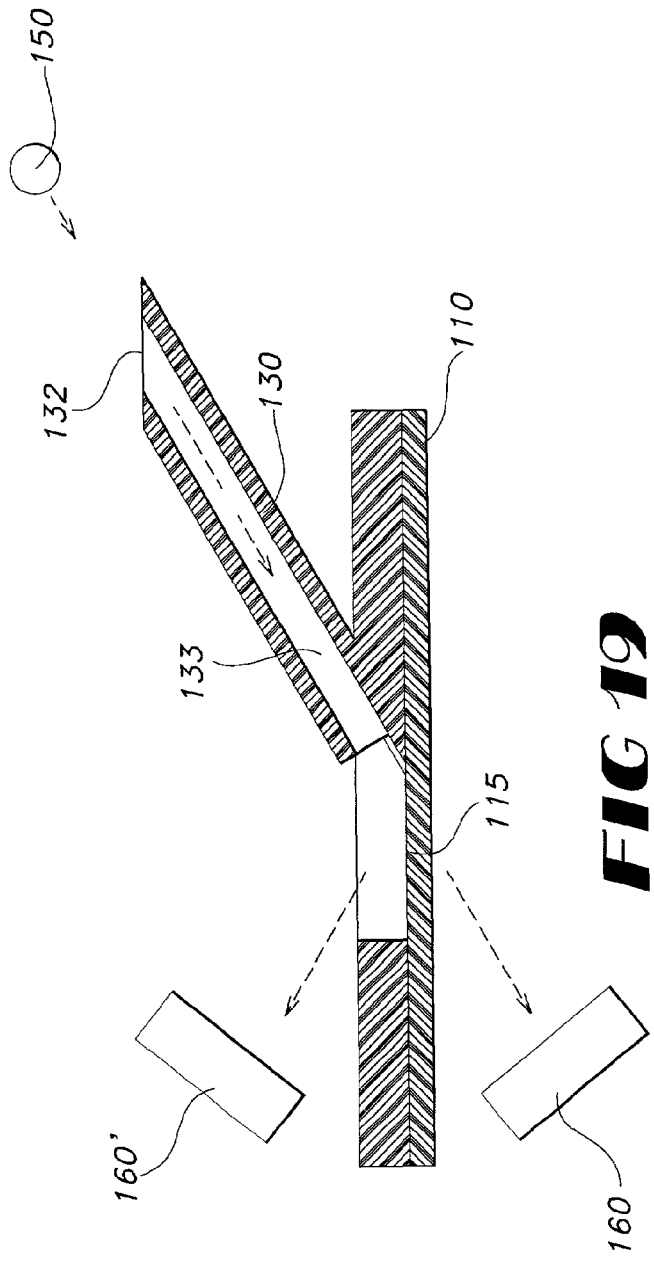
FIG. 19 is a cross-sectional view of sixth diagnostic device taken along line 19 of FIG. 20.

The present invention also provides a system for detecting the presence of an analyte. In a desirable embodiment, a system of the present invention comprises a light source 150 that can be directed through the interior 134 of the capillary 130 to the binder-printed surface as illustrated in FIGS. 4, 4A, 12A and 19 or through another opening 152 or window that transmits light as illustrated in FIGS. 8, 12, 16 and 21. In the embodiment illustrated in FIG. 4, light source 150 is configured in a system or is otherwise directed to align with interior passage 134 so that light is transmitted through the test surface to produce a diffraction image. Light source 150 may be any source of light including ambient light. However, it is desirable that the light source is a focused light source such a laser or is focused via the use of a mechanical device such as a pinhole. It may also be further desirable that the light source or focused light source is a monochromatic light source, that is a light source that produces light of one wavelength. The wicking agent 114 may include an opening 116 through which light may be directed to the test surface. A system of the present invention may also further include a detector 160 for determining if diffraction occurs and, thus, analyte is detected. The detector 160 may be any device that measures light intensity or any device that can be used to determine between diffraction and non-diffraction. Examples of detectors or devices that may be used for detection include photodiodes, array detectors and other devices or means of measuring the intensity of the diffracted light. Diffraction may be detected by a human in embodiments that produce a visible diffraction pattern. Systems of the present invention may further include a housing (not illustrated) for configuring and protecting various components of a system and to provide a unified, consolidated system for detecting an analyte.

Detection of a target analyte in a sample may be determined by measuring a difference in diffraction of light from the binder-printed surface before and after the binder-printed surface is exposed to a sample. In most instances, the presence of analyte will be detected by determining if the test surface diffracts light or other electromagnetic radiation after the test surface is exposed to a sample. However, it is possible that the presence of analyte may be measured by either an increase or a decrease in diffraction or by lack of diffraction if a binder-printed surface is provided that initially diffracts electromagnetic radiation and will diffract electromagnetic radiation to a greater or a lesser extent, respectively, when analyte is bound, reacted or otherwise associated with binder that is printed on the surface.

Devices may be provided that direct sample to more than one test site. The multiple test loci may be provided on the same surface or film or on separate surfaces or films. An example of a device that directs a sample to two test loci is illustrated in FIGS. 1A-4A. The device illustrated in FIGS. 1A-4A comprises a means 120 for directing a sample to a test surface that comprises two capillaries 130 (i.e., channels through which a fluid is capable of flowing via capillary action) for directing a sample to two test loci (not shown). Each capillary comprises a first opening 132 an interior passage 134 and a second opening 136 that is in fluid communication with a test site. A device that comprises two test loci may be used to test a sample for two different analytes, test a sample for the same analyte at two different test sites, thus, providing a back-up test or test a sample at one locus and the other, control, locus may be used a base line for determining diffraction versus non-diffraction. For example, a second test locus can be used as a control locus and can be used to confirm that the device is functioning correctly. Alternatively, or in addition, the second test locus can be as a control test pattern by providing a benchmark diffraction pattern that must be achieved in order to a test result to be considered positive for the presence of analyte. A diagnostic test kit may include control samples that contain one or more samples of the target analyte(s). Thus, control sample may be used to confirm that the device functions properly. A kit may further comprise one or more solutions to assist in conducting the methods of the invention, for example, solutions for diluting samples, solutions for incubating samples, solutions for rinsing samples and solutions comprising one or more blocking agents. Desired solutions, control and otherwise, are sterile and free of substances that may interfere with detection of analyte.

Figure 6:
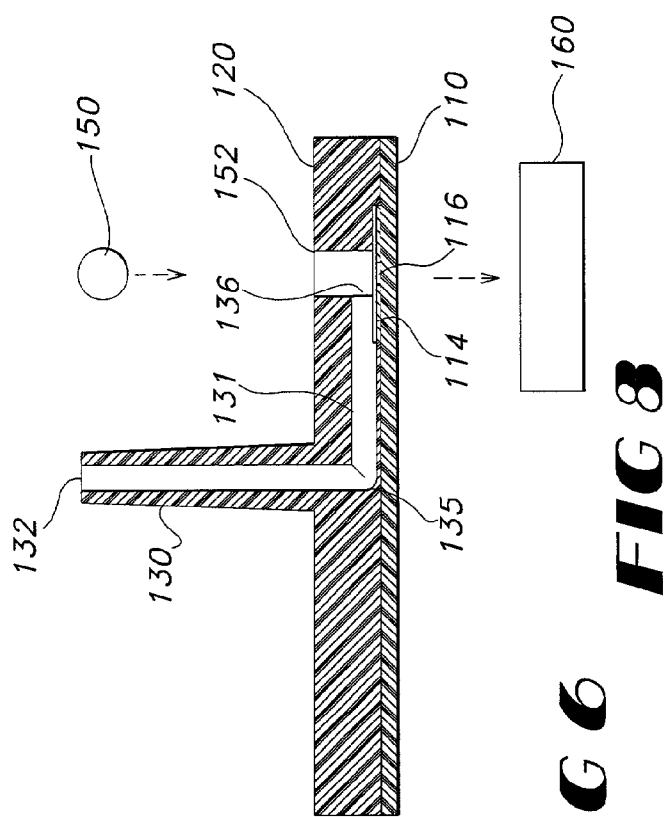
FIG. 6 is an exploded, perspective view of the third diagnostic device.

In the examples illustrated in FIGS. 1-4 and 1A-4A, the diagnostic devices are illustrated showing a means 120 for directing a sample to the test surface comprises a capillary that is generally linear. However, a means 120 for directing a sample to the diagnostic test surface may be nonlinear. Means 120 for directing a sample to the diagnostic test surface that are curved or that comprise one or more turns or branches are illustrated in FIGS. 5-8, 13-16 and 21. The diagnostic devices illustrated in FIGS. 5-16 provide diagnostic devices having a means 120 for directing a sample to a test surface that direct a portion of a sample to more than one test site. These devices with multiple test loci can provide for the testing of one or more analytes by incorporating one or more binders specific to an analyte at the different test surfaces or at different portions or locations of a film surface. For example, a diagnostic device may be provided that divides a sample of blood and tests one portion of a sample at a first locus for one analyte, for example luetenizing hormone (LH) and tests another portion of the sample at a second, different test locus for another analyte, for example follicle stimulating hormone (FSH). Additional analytes or classes of analytes may be tested for at additional test loci.

A system of the present invention may comprise multiple light sources and detectors for detecting analytes at multiple test loci or may comprise only one light source and/or one detector and move the sample or the light source and/or detector to test for analyte at the other test loci. For example, light source 150 and detector 160 may be moved relative to the device 100 or film 110 from to the positions illustrated as 150' and 160' as illustrated in FIG. 4A so as to direct the light source to an other test loci. Alternatively, a second light source 150' and a second detector 160' may be provided.

Those skilled in the art will appreciate that other modifications may be made to adapt the diagnostic devices, methods and systems of the present invention. A few modifications and adaptations are illustrated herein. FIGS. 5-8 illustrate a diagnostic device 100 in which the means 120 for directing a sample to a test surface divides a sample into two portions and directs the portions to two test loci that are located on the surface 112 of film 110 located under and in contact with wicking agent 114. The means 120 for directing a sample to a test surface illustrated in FIGS. 5-8 comprises one capillary 130 that connects to two diverging capillaries or channels 131 and 131 at intersection 135. Each capillary channel extends to an opening 136 that is proximate a test locus. The test loci are printed with a binder and may further include a wicking agent, more specifically a layer comprising a wicking agent 114. The layer of wicking agent may further comprise an opening 116 through which electromagnetic radiation may be directed to the test locus and binder printed surface to determine if diffraction occurs. A device of the present invention may include additional diverging channels and test loci.

The devices of the present invention may also include one or more openings 152 or windows that transmit light or other electromagnetic radiation over each test locus 115 so that light or electromagnetic radiation can be directed to and transmitted through or reflected from the binder-printed surface. The device illustrated in FIGS. 5-8 is used by bringing a liquid sample into contact with opening 132. The sample is then directed through interior passage 134 to intersection 135 where the sample diverges and a portion of the sample is directed to each of channels 131 and 131 and finally to the second openings 136 and 136. The layers of wicking agent 114 then draw a portion of the sample from each of the second openings 136 and spread the sample across the respective portion of the device that is printed with the binder(s). The sample, or at least a portion of the sample, then contacts the portion of the device that is printed with the binder antibody so that analyte that may be contained in the sample can bind, react or otherwise associate with the binder that is printed on the surface 112. Light 150 or other electromagnetic radiation may then be directed through opening 152 to determine if the surface diffracts electromagnetic radiation either by reflecting electromagnetic radiation off of the surface 112 or transmitting electromagnetic radiation through the surface 112. Diffraction may be detected by a viewer, a person or with the aid of a detector 160. Analyte testing at additional test loci may be accomplished by rotating the device 100 relative to the light source 150 and detector 160 or by providing additional light sources and/or detectors.

Figure 20:
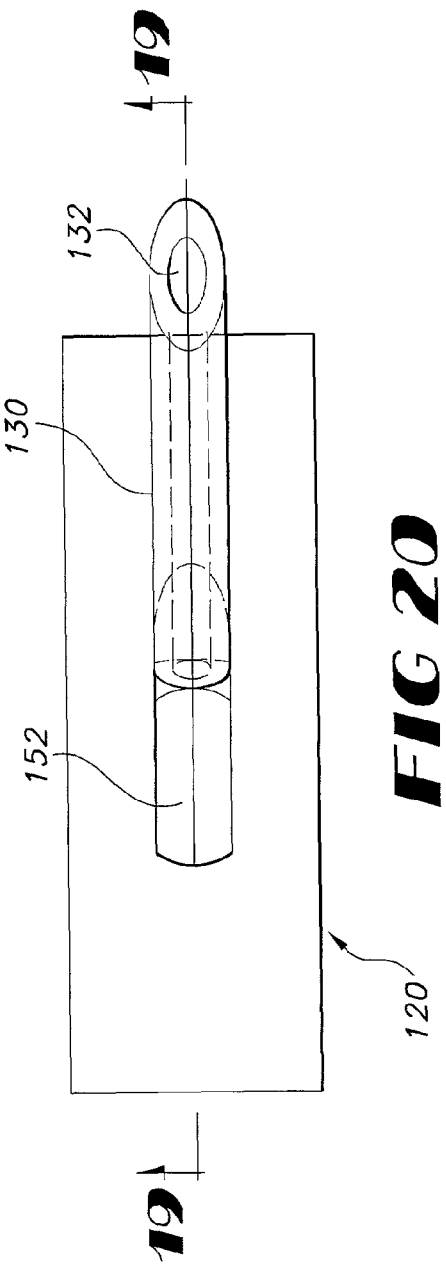
FIG. 20 is a plan view of the sixth diagnostic device.

In the examples illustrated in FIGS. 1-4, the diagnostic system is illustrated showing a means 120 for directing a sample to a test surface that is generally perpendicular to the test strip and the binder-printed, test surface. However, means 120 for directing a sample to the diagnostic test surface is not required to be perpendicular to the test surface and may be configured at an angle to the test surface, that is at an angle greater than or less than 90° to the test surface. Examples of such devices are illustrated in FIGS. 9-12 and 17-20. In the examples illustrated in FIGS. 9-12 and 12A, the diagnostic device comprises a means for directing a sample to a test surface 120 that divides a sample into three portions and which directs a portion of the sample to each of the three test loci 115 located on the surface 112 of film 110. In these examples, the means 120 for directing a sample to a test surface further comprises a well 125 for initially receiving a sample. A sample may be deposited into well 125. The well 125 is connected to a plurality of passages, in this example three passages 131 via passage 134. Passage 134 diverges and extends to three passages 131 that then lead to three different test loci 115 so that a sample is divided into three portions and directed to the three test loci 115. The three different test loci 115 may test for three different analytes, two different analytes with one control, three test loci for one analyte or any other combination of analyte(s) and control(s) as may be desired. In an optional embodiment, the device and system of the present invention further comprise an additional opening 152 over each test locus 115 so that a light 150 can be directed transmitted through the opening to the test locus and reflected from the binder-printed surface (as illustrated on the right side of FIG. 16) or transmitted through the binder-printed surface (as illustrated on the left side of FIG. 16). Optional detectors 160 are illustrated in both the transmitted and reflected modes of detection. Additional openings are not required and light 150 may be directed through the passages 134 to determine if the test surfaces diffract light. The light source or the passages or openings may be rotated or moved to align the light source with a particular passage or opening. Alternatively, a light source may be split and redirected or multiple light sources may be provided; one light source for each opening.

FIGS. 13-16 illustrate yet another example of the present invention. In this illustrated example, the well 125 extends into conduit 134 that diverges into four conduits 131 at intersection 135 and leads to four different test loci 115 so that a sample is divided into four portions for testing at the four test loci 115. Again, the four different test loci 115 may test for replicate measurements for one analyte, four different analytes, three different analytes at three different test loci with one control test site, two different analytes at two different test loci with two control test loci or otherwise. In an optional desirable embodiment, the device and system of the present invention further comprise an additional opening 152 over each test locus 115 so that light can be directed to and transmitted or reflected through each opening 152.

FIGS. 17-20 illustrate yet another example of the present invention. In this illustrated example, the device 100 comprises a means for directing 120 that includes a capillary 130 that is angled to facilitate the transmission or reflection of electromagnetic radiation used for detection. The means for directing 120 further includes a first opening 132 that can be beveled to more readily receive a liquid sample. The capillary 130 directs the liquid sample from the beveled opening 132 to the binder-printed surface to test for analyte in the sample. The test surface and device may or may not further include an optional wicking agent layer and/or optional diffraction enhancing elements. The device may also further comprise an opening 152 or a window that transmits light or other electromagnetic radiation through which light 150 may be reflected or transmitted.

After the sample contacts the test surface and is given sufficient incubation time to bind with the test surface, the presence of binding and the accompanying diffraction can be ascertained via the use of a detector 160 that is positioned to receive and detect radiation that is reflected from the surface of film (position 160') or transmitted through film 110 (position 160). Specifically, a detector 160 may be positioned at the location illustrated at the top of FIG. 19 to receive and detect reflected radiation and at the location illustrated at the bottom of FIG. 19 to receive and detect transmitted radiation. Alternatively, the presence of a diffraction pattern can be ascertained visually by an individual without the use of a detector or an analyzer.

Yet another example of a diagnostic device of the present invention is illustrated in a cross-sectional view in FIG. 21. In the example illustrated in FIG. 21, the diagnostic device 100 includes means 120 for directing a sample to a test surface that further includes an opening 132 for receiving a sample that is in fluid communication with a film 110 upon which a binder is printed via passageway 134. A layer of wicking agent 114 and diffraction enhancing elements may also be included on the binder-printed surface. Optional absorbent material 140 may be provided to aid in directing liquid sample to the binder-printed test surface or to help remove excess sample from the binder-printed surface. The device may also include a window 170 through which light 150 or other electromagnetic radiation may be directed to the binder-printed surface and the layer of wicking agent may also include a hole 116 through which light or other electromagnetic radiation may be directed. Diffraction may be detected in the transmitted mode, light and detector positions 150 and 160, or reflected mode, light and detector positions 150' and 160'.

While various patents and other reference materials have been incorporated herein by reference, to the extent there is any inconsistency between incorporated material and that of the written specification, the written specification shall control. In addition, while the invention has been described in detail with respect to various specific examples, illustrations and embodiments thereof, it will be apparent to those skilled in the art that various alterations, modifications and other changes may be made to the invention without departing from the spirit and scope of the present invention. It is therefore intended that the appended claims cover all such modifications, alterations and other changes.

EXAMPLE 1

A gold-coated plastic film (e.g., ~10 nm thick gold on one side of 3-7 mil MYLAR film sufficient to give <20 ohms/square resistance reading, supplied by CP Films, Inc.; Canoga Park, Calif.) was treated with a blocking agent, beta casein, by soaking the film in a 5 mg/mL solution of beta casein. The solution of beta casein was prepared by dissolving 25 mg of beta casein in 5 mL phosphate buffered saline (PBS) at pH 7.2. After exposure to the beta casein solution for 10 minutes, the film was rinsed with distilled water and dried in an air stream. The treated film, gold-side up, was then contact printed with a thiolated, monoclonal anitibody to C-reactive protein (e.g., Biospacific monoclonal anti-C-reactive protein, Clone # A58040136P) in 10-micron diameter circles on the film to provide a patterned x,y-array of the antibody on the film. Next, a suspension of antibody-conjugated (Biospacific monoclonal anti-C-reactive protein, Clone #A58110228P) latex microparticles, 0.3 micron diameter at 1.25% solids, was resuspended into a buffer containing 5-10 wt % sucrose and mouse IgG (or optionally, Heterophilic Blocking Reagent, HBR, Cat #3KC534 from Scantibodies, Santee, Calif.). An 11 microliter aliquot of a suspension of antibody-labeled latex microparticles was added by pipetting it on top of the antibody-patterned film. The film with particles was placed in a freezer at ~−20° C. until the particle suspension was frozen (typically ≧1 hour), and then freeze-dried (~5-20 mm Hg, using Labconco Model #77500 freeze drying unit with a vacuum pump to dry the antibody-labeled microparticles on the patterned film surface. A wicking agent (e.g., 0.1 micron pore size Duropore Cat #VVHP04700 from Millipore; Bedford, Mass.) was placed on top of the surface of the microparticle-coated and patterned film (still gold-side up on film). The wicking agent had a 1.6 mm hole cut out of its center (e.g., using a die punch) prior to placing it on the film. This small area (which can range in diameter, typically between 1-3 mm) of the film was not coated with wicking agent to provide a viewing area for diffraction from the sample. The above provided a one-step diagnostic device.

For testing, 34 microliters of sample (e.g., 3.4 µL whole blood with EDTA as anti-coagulant, diluted in 30.6 µL PBS with 0.3% Triton) was added to the top of the film by pipetting this such that the droplet went in the center of the circular area without wicking agent (due to the hole punched out from its center). This caused the blood sample to be slowly, radially wicked away from the gold-coated surface as it was taken in or absorbed by the wicking agent. After the liquid sample had been absorbed by the wicking agent, a clear path for viewing diffraction (or lack thereof) remained through the hole cut from the wicking agent.

Binding was determined microscopically and quantified by determining the percentage within the viewing area (e.g., 1.6 mm) that showed binding of particles in the 10-micron diameter patterned areas. Typically, a 100× magnification was done for this "percent coverage" determination. Also, diffraction was monitored by passing a red helium-neon laser (wavelength 633 nm) through the film.

EXAMPLE 2

A gold-coated plastic film as described in Example 1, gold-side up, was treated with a blocking agent, e.g., 5 mg/mL beta casein for 10 minutes, rinsed, and dried as described in Example 1. The treated film, gold-side up, was then contact printed with a thiolated, monoclonal antibody to C-reactive protein (e.g., Fitzgerald monoclonal anti-luteinizing hormone beta subunit, Catalog #10-L15) in 10-micron diameter circles on the film to provide a patterned x,y-array of the antibody on the film. Next, a suspension of antibody-conjugated (e.g., Fitzgerald monoclonal anti-luteinizing hormone alpha subunit, Catalog #10-L10) latex microparticles, 0.3 micron diameter at 1.25% solids, was resuspended into a buffer containing 10% sucrose and mouse IgG (or optionally, Heterophilic Blocking Reagent, HBR, Cat #3KC534 from Scantibodies, Santee, Calif.). A suspension of antibody-labeled latex microparticles was added by pipetting it on top of the antibody-patterned film (typically an aliquot of 4-11 microliters was used of the 1.25% solids conjugated particle sample). The film with particles was frozen and then freeze-dried as described in Example 1. A wicking agent (e.g., 0.6 micron pore size polypropylene, Cat #AN0604700 from Millipore; Bedford, Mass.) was placed on top of the surface of the microparticle-coated and patterned film (still gold-side up on film). The wicking agent had a 1.4 mm hole cut out of its center (e.g., using a die punch) prior to placing it on the film. This small area (which can range in diameter, typically between 1-3 mm) of the film was not coated with wicking agent to provide a viewing area for diffraction from the sample.

This assembly was then placed in a plastic strip housing with capillary tube (e.g., refer to FIGS. 1-4 for exemplary formats) such that there was essentially no gap between the sample film and the capillary tube. Care was taken such that the hole in the wicking agent aligned with the hole in the capillary tube. Also, a hole was cut into the housing of the backing in order to allow a full light path through the capillary tube, through the diffractive film sample, and through the hole placed in the housing.

For testing, 11-34 microliters of the sample was used (e.g., 34 µL of diluted whole blood if 11 microliters particles had been dried on the film surface, or 11 µL diluted blood if only 4 microliters of particles had been dried on the film). The sample was added to the top of the capillary tube tip such that it was pulled into the tube by capillary action and then brought down to the diffraction film surface. The blood sample was then slowly wicked away from the gold-coated surface as it was taken in or absorbed by the wicking agent. After the liquid sample had been absorbed by the wicking agent, diffraction could be detected by shining a laser light through the capillary tube such that it was transmitted through the path created by alignment of the holes in the device. If the sample was positive for analyte (e.g., LH in this example), then a diffraction image could be detected as it was transmitted through the tube.

EXAMPLE 3

A gold-coated plastic film as described in Example 1, gold-side up, was contact printed with a thiolated, monoclonal anitibody to C-reactive protein (e.g., Biospacific monoclonal anti-C-reactive protein, Clone #A58040136P) in 10-micron diameter circles on the film to provide a patterned x,y-array of the antibody on the film. Next, the printed film was treated with a blocking agent, beta casein, by soaking the film in a 5 mg/mL solution of beta casein. The solution of beta casein was prepared by dissolving 25 mg of beta casein in 5 mL phosphate buffered saline (PBS) at pH 7.2. After exposure to the beta casein solution for 10 minutes, the film was rinsed with distilled water and dried in an air stream.

Next, a suspension of antibody-conjugated (Biospacific monoclonal anti-C-reactive protein, Clone #A58110228P) latex microparticles, 0.3 micron diameter at 1.25% solids, was resuspended into 5% sucrose and HBR reagent (Heterophilic Blocking Reagent, Cat #3KC534 from Scantibodies, Santee, Calif.). The film and 11 microliters of a suspension of antibody-labeled latex microparticles were added by pipetting it on top of the antibody-patterned film. The film with particles was placed in a freezer at ~−20° C. until the particle suspension was frozen (typically ≧1 hour), and then freeze-dried (~5-20 mm Hg, using Labconco Model #77500 freeze drying unit with a vacuum pump to dry the antibody-labeled microparticles on the patterned film surface. A wicking agent (e.g., 0.1 micron pore size Duropore Cat #VWHP04700, from Millipore, Bedford, Mass.) was placed on top of the surface of the microparticle-coated and patterned film (still gold-side up on film). The wicking agent had a 1.6 mm hole cut out of its center (e.g., using a die punch) prior to placing it on the film. This small area (which can range in diameter, typically between 1-3 mm) of the film was not coated with wicking agent to provide a viewing area for diffraction from the sample. The above provided a one-step diagnostic device.

Testing and subsequent measurements were done as described in Example 1. Optionally, testing was done using whole blood that had been diluted with buffer containing 3% Triton X-100. For example, 1.1 microliters of EDTA whole blood was mixed with 9.9 µL of diluent containing 3% Triton; this 11 µL diluted whole blood was added to the top of the film by pipetting it such that the droplet went in the center of the circular area without wicking agent (due to the hole punched out from its center). This caused the blood sample to be slowly, radially wicked away from the gold-coated surface as it was taken in or absorbed by the wicking agent. After the liquid sample had been absorbed by the wicking agent, a clear path for viewing diffraction (or lack thereof) remained through the hole cut from the wicking agent.

We claim:

1. A diffraction-based assay device for detecting the presence of an analyte, the device comprising:
   a substrate that comprises a polymer film, wherein a first binder is present on the substrate in a pattern;
   a fluidic guide with a first end and a second end in direct communication with a wicking agent, wherein the first end of the fluidic guide defines an opening therein for sample application and includes at least one channel through which a fluid test sample is capable of flowing via capillary action to the second end,
   wherein the wicking agent is capable of receiving the fluid test sample from the second end of the fluidic guide and thereafter facilitating contact of the fluid sample with the binder on the substrate; and
   an electromagnetic radiation source that is configured to direct electromagnetic radiation to the substrate through the first end of the fluidic guide to the opening to generate a diffraction pattern proximate an area of the substrate defined by the second end of the guide.

2. The diffraction-based device of claim 1, wherein the wicking agent defines an opening through which the electromagnetic radiation is capable of passing.

3. The diffraction-based device of claim 1, wherein a second binder is also present on the substrate.

4. The diffraction-based device of claim 1, wherein the first opening is beveled.

5. The diffraction-based device of claim 1, wherein the fluidic guide is generally linear.

6. The diffraction-based device of claim 1, wherein the fluidic guide has one or more turns or branches.

7. The diffraction-based device of claim 1, wherein the fluidic guide is positioned generally perpendicular to the substrate.

8. The diffraction-based device of claim 1, wherein the fluidic guide is in communication with a well, the well initially receiving the fluid sample.

9. The diffraction-based device of claim 1, wherein the fluidic guide is positioned directly adjacent to and in fluid communication with the wicking agent.

10. The diffraction-based device of claim 1, wherein the substrate comprises the metal coating.

11. The diffraction-based device of claim 1, further comprising a detector for detecting the diffraction pattern.

12. The diffraction-based device of claim 1, wherein the diffraction pattern is generated only upon exposure of the substrate to the analyte.

13. The diffraction-based device of claim 1, wherein the polymer film is generally transparent to the electromagnetic radiation.

14. A diffraction-based assay device for detecting the presence of an analyte, the device comprising:
   a substrate that comprises a polymer film, wherein a first binder is present on the substrate in a pattern;
   a fluidic guide with a first end and a second end in direct communication with a wicking agent, wherein the first end of the fluidic guide defines an opening therein for sample application and includes at least one channel through which a fluid test sample is capable of flowing via capillary action to the second end;
   means for venting pressure to facilitate movement of the fluid test sample in a direction of the substrate;
   wherein the wicking agent is capable of receiving the fluid test sample from the second end of the fluidic guide and thereafter facilitating contact of the fluid sample with the binder on the substrate; and
   an electromagnetic radiation source that is configured to direct electromagnetic radiation to the substrate through the first end of the fluidic guide to generate a diffraction pattern proximate an area of the substrate defined by the second end of the guide.

15. The diffraction based device of claim 14, wherein the means for venting pressure is a pressure vent disposed proximate the wicking agent in communication with the wicking agent and external atmosphere.

16. The diffraction-based device of claim 14, wherein the substrate further comprises a metal coating.

17. The diffraction-based device of claim 1, wherein the substrate further comprises a metal coating.

18. A diffraction-based assay device for detecting the presence of an analyte, the device comprising:
   a substrate that comprises a polymer film, wherein a binder is present on the substrate in a pattern;
   a fluidic guide with a first and second end in direct communication with the wicking agent, wherein the first end of the fluidic guide receives a fluid test sample and includes at least one channel through which the fluid test sample is capable of flowing via capillary action to the second end,
   the wicking agent defining a hole therethrough and capable of receiving the fluid test sample from the second end of the fluidic guide and thereafter facilitating contact of the fluid sample with the binder on the substrate; and
   an electromagnetic radiation source that is configured to direct electromagnetic radiation to the substrate through the first end of the fluidic guide to generate a diffraction pattern proximate an area of the substrate defined by the second end of the guide.

* * * * *